US012595294B2

(12) United States Patent
Pompiati et al.

(10) Patent No.: US 12,595,294 B2
(45) Date of Patent: Apr. 7, 2026

(54) METHODS TO DECREASE IMPURITIES FROM RECOMBINANT PROTEIN MANUFACTURING PROCESSES

(71) Applicant: HOFFMANN-LA ROCHE INC., Little Falls, NJ (US)

(72) Inventors: Marc Pompiati, Penzberg (DE); Christoph Feistl, Penzberg (DE)

(73) Assignee: Hoffmann-La Roche Inc., Little Falls, NJ (US)

( * ) Notice: Subject to any disclaimer, the term of this patent is extended or adjusted under 35 U.S.C. 154(b) by 784 days.

(21) Appl. No.: 17/812,145

(22) Filed: Jul. 12, 2022

(65) Prior Publication Data

US 2023/0049176 A1    Feb. 16, 2023

Related U.S. Application Data

(63) Continuation of application No. PCT/EP2021/050809, filed on Jan. 15, 2021.

(51) Int. Cl.
*C07K 16/06* (2006.01)
*C07K 1/34* (2006.01)

(52) U.S. Cl.
CPC .............. *C07K 16/065* (2013.01); *C07K 1/34* (2013.01); *C07K 2317/31* (2013.01); *C07K 2317/35* (2013.01); *C07K 2319/30* (2013.01)

(58) Field of Classification Search
CPC .................................................... C07K 16/065
See application file for complete search history.

(56) References Cited

U.S. PATENT DOCUMENTS

| | | | |
|---|---|---|---|
| 4,676,980 A | 6/1987 | Segal | |
| 4,882,013 A | 11/1989 | Turner et al. | |
| 5,591,828 A | 1/1997 | Bosslet | |
| 5,731,168 A | 3/1998 | Carter | |
| 9,249,182 B2 | 2/2016 | Herigstad et al. | |
| 10,342,876 B2 | 7/2019 | Bak et al. | |
| 11,518,781 B2 | 12/2022 | Koehnlein | |
| 2008/0069820 A1 | 3/2008 | Fuh | |
| 2011/0207196 A1 | 8/2011 | Koehler et al. | |
| 2013/0090389 A1 | 4/2013 | Vitins et al. | |
| 2014/0010820 A1 | 1/2014 | Wang et al. | |
| 2014/0309403 A1 | 10/2014 | Brown et al. | |
| 2016/0176921 A1 | 6/2016 | Rajendran et al. | |
| 2016/0272674 A1 | 9/2016 | Althouse et al. | |
| 2016/0320909 A1 | 11/2016 | Eim et al. | |
| 2017/0073396 A1 | 3/2017 | Bataille et al. | |

| | | |
|---|---|---|
| 2017/0189536 A1 | 7/2017 | Connolly et al. |
| 2018/0360856 A1 | 12/2018 | Holmes et al. |
| 2018/0369258 A1 | 12/2018 | Holmes et al. |
| 2022/0135620 A1 | 5/2022 | Seay et al. |
| 2022/0194980 A1 | 6/2022 | Leiss et al. |
| 2023/0047100 A1 | 2/2023 | Arcadu et al. |

FOREIGN PATENT DOCUMENTS

| | | |
|---|---|---|
| EP | 0404097 A2 | 12/1990 |
| WO | 199311161 A1 | 6/1993 |
| WO | 199850431 A2 | 11/1998 |
| WO | 199850431 A3 | 1/1999 |
| WO | 200177342 A1 | 10/2001 |
| WO | 2003/100080 A1 | 12/2003 |
| WO | 2006/044532 A1 | 4/2006 |
| WO | 2008024715 A2 | 2/2008 |
| WO | 2008024715 A3 | 11/2008 |
| WO | 2009080251 A1 | 7/2009 |
| WO | 2009080252 A1 | 7/2009 |
| WO | 2009080253 A1 | 7/2009 |
| WO | 2009089004 A1 | 7/2009 |
| WO | 2010048192 A2 | 4/2010 |
| WO | 2010048192 A3 | 6/2010 |
| WO | 2010112193 A1 | 10/2010 |
| WO | 2010115589 A1 | 10/2010 |
| WO | 2010136172 A1 | 12/2010 |
| WO | 2010145792 A1 | 12/2010 |
| WO | 2011034605 A2 | 3/2011 |
| WO | 2011034605 A3 | 8/2011 |
| WO | 2011/150110 A1 | 12/2011 |
| WO | 2013/009491 A2 | 1/2013 |
| WO | 2013026831 A1 | 2/2013 |
| WO | 2013028330 A2 | 2/2013 |
| WO | 2013028330 A3 | 8/2013 |
| WO | 2013177115 A2 | 11/2013 |
| WO | 2014/004281 A1 | 1/2014 |
| WO | 2013177115 A3 | 2/2014 |
| WO | 2015/023468 A1 | 2/2015 |
| WO | 2015031899 A1 | 3/2015 |
| WO | 2015/077605 A1 | 5/2015 |
| WO | 2015095539 A1 | 6/2015 |
| WO | 2015150447 A1 | 10/2015 |

(Continued)

OTHER PUBLICATIONS

Al-Lazikani, B. et al. (1997). "Standard Conformations for the Canonical Structures of Immunoglobulins," J. Mol. Biol. 273:927-948.

(Continued)

*Primary Examiner* — Prema M Mertz

(74) *Attorney, Agent, or Firm* — MORRISON & FOERSTER LLP

(57) ABSTRACT

The invention relates to a method of reducing the amount of non-aggregate produce-related impurities (NAPRIs) in a buffered solution of monoclonal antibodies (mAbs), involving the use of a synthetic depth filter. The invention may be of use in the purification of monoclonal 5 antibodies.

15 Claims, 6 Drawing Sheets

(56) References Cited

FOREIGN PATENT DOCUMENTS

| | | | |
|---|---|---|---|
| WO | 2015/198320 | A1 | 12/2015 |
| WO | 2016016299 | A1 | 2/2016 |
| WO | 2016/106291 | A1 | 6/2016 |
| WO | 2016172485 | A2 | 10/2016 |
| WO | 2016172485 | A3 | 12/2016 |
| WO | 2017/031476 | A2 | 2/2017 |
| WO | 2017027861 | A1 | 2/2017 |
| WO | 2017/095062 | A1 | 6/2017 |
| WO | 2017218977 | A2 | 12/2017 |
| WO | 2017218977 | A3 | 1/2018 |
| WO | 2018035025 | A1 | 2/2018 |
| WO | 2018170488 | A1 | 9/2018 |
| WO | 2018200430 | A1 | 11/2018 |
| WO | 2019191416 | A1 | 10/2019 |
| WO | 2020006266 | A1 | 1/2020 |
| WO | 2020023566 | A1 | 1/2020 |
| WO | 2020/159838 | A1 | 8/2020 |
| WO | 2020200980 | A1 | 10/2020 |
| WO | 2020227144 | A1 | 11/2020 |
| WO | 2021144422 | A1 | 7/2021 |
| WO | 2022094116 | A1 | 5/2022 |

OTHER PUBLICATIONS

Atwell, S. et al. (1997). "Stable Heterodimers From Remodeling The Domain Interface Of A Homodimer Using A Phage Display Library," J. Mol. Biol. 270 (1):26-35.

Brennan, M. et al. (Jul. 5, 1985). "Preparation of Bispecific Antibodies by Chemical Recombination of Monoclonal Immunoglobulin G1 Fragments," Science 229:81-83.

Chadd, H.E. et al. (2001). "Therapeutic Antibody Expression Technology," Curr. Opin. Biotechnol 12:188-194.

Charlton, H.R. (Jan. 1, 1999). "Characterisation of a Generic Monoclorial Antibody Harvesting System For Adsorption of DNA By Depth Filters and Various Membranes," Bioseparation 8:281-291, 27 pages.

Chiu, J. et al. (May 2017). "Knockout of a Difficult-To-Remove CHO Host Cell Protein, Lipoprotein Lipase, For Improved Polysorbate Stability In Monoclonal Antibody Formulations," Biotechnology And Bioengineering 114(5):1006-1015, 22 pages.

Chothia, C. et al. (1987). "Canonical Structures for the Hypervariable Regions of Immunoglobulins," J. Mol. Biol. 196:901-917.

Chothia, C. et al. (Dec. 21/28, 1989). "Conformations of Immunoglobulin Hypervariable Regions," Nature 342(6252):877-883.

Chothia, C. et al. (Dec. 5, 1985). "Domain Association In Immunoglobulin Molecules. The Packing Of Variable Domains," J. Mol. Biol. 186(3):651-663.

Extended European Search Report, dated Jun. 25, 2022, for European Patent Application No. 20151994.9, 9 pages.

Giese, G. et al. (2018, e-pub. Nov. 29, 2017). "Bispecific Antibody Process Development: Assembly and Purification of Knob and Hole Bispecific Antibodies," Biotechnol. Prog. 34(2):397-404. Abstract.

Gruber, M. et al. (1994). "Efficient Tumor Cell Lysis Mediated by a Bispecific Single Chain Antibody Expressed in *Escherichia Coli*," J. Immunol. 152:5368-5374.

Hall, T. et al. (May 2006, e-pub. Apr. 5, 2016). "Polysorbates 20 and 80 Degradation by Group XV Lysosomal Phospholipase A2 Isomer XI in, Monoclonal Antibody Formulations," Journal Of Pharmaceutical Sciences 105(5):1633-1642.

Holliger, P. et al. (Sep. 2005) "Engineered Antibody Fragments and The Rise Of Single Domains," Nat. Biotechnol. 23(9):1126-1136.

Hollinger, P. et al. (Jul. 1993). "Diabodies": Small Bivalent And Bispecific Antibody Fragments, Proc. Natl. Acad. Sci. USA 90:6444-6448.

International Preliminary Report on Patentability, issued Jul. 19, 2022, for PCT Application No. PCT/EP2021/050809, filed Jan. 15, 2021, 8 pages.

International Preliminary Report on Patentability, issued Nov. 2, 2021, for PCT Application No. PCT/US2020/031164, filed May 1, 2020, 9 pages.

International Search Report and Written Opinion, mailed Jul. 17, 2020, for PCT Application No. PCT/US2020/031164, filed May 1, 2020, 17 pages.

International Search Report and Written Opinion, mailed Mar. 23, 2021, for PCT Application No. PCT/EP2021/050809, filed Jan. 15, 2021, 11 pages.

International Search Report and Written Opinion, mailed Mar. 31, 2022 for PCT Application No. PCT/US2021/057100, filed Oct. 28, 2021, 24 pages.

Invitation To Pay Additional Fees, mailed Feb. 10, 2022, for PCT Application No. PCT/US2021/057100, filed Oct. 28, 2021, 21 pages.

Jones, P.T. et al. (May 29, 1986). "Replacing the Complementarity-Determining Regions in a Human Antibody With Those From a Mouse," Nature 321:522-525.

Kabat, E.A. et al. (1991). Sequences of Proteins of Immunological Interest, 5th ed., Public Health Service, National Institutes of Health, Bethesda, MD. TOC, 21 pages.

Klein, C. et al. (Jun. 10, 2016, e-pub. Jul. 11, 2016). "The Use of CrossMab Technology for the Generation of Bi- and Multispecific Antibodies," MABS 8(6):1010-1020.

Kostelny, S.A. et al. (Mar. 1, 1992). "Formation of a Bispecific Antibody By The Use of Leucine Zippers," J. Immunol. 148(5):1547-1553.

Liu, H. et al. (Sep./Oct. 2010). "Recovery and Purification Process Development for Monoclonal Antibody Production," mAbs 2(5):480-499.

Marichal-Gallardo, P.A. et al. (2012, e-pub. Jun. 26, 2012). "State-Of-The-Art In Downstream Processing Of Monoclonal Antibodies: Process Trends In Design and Validation," Biotechnology Progress 28(4):899-916.

Merchant, A. M. et al. (Jul. 1998). "An Efficient Route To Human Bispecific IgG," Nature Biotechnology 16:677-681.

Milstein, C. et al. (Oct. 6, 1983). "Hybrid Hybridomas and Their Use In Immunohistochemistry," Nature 305:537-540.

Morrison, S.C. et al. (Nov. 1984). "Chimeric Human Antibody Molecules: Mouse Antigen-Binding Domains With Human Constant Region Domains," Proc. Natl. Acad. Sci. USA 81:6851-6855.

Nguyen, H.C. et al. (May 11, 2018). "Improved HCP Reduction Using a New, All-Synthetic Depth Filtration Media Within an Antibody Purification Process," Biotechnology Journal 14(11):1700771, 11 pages.

Onur, A. et al. (Sep. 12, 2018). "Multi-Layer Filters: Adsorption and Filtration Mechanisms for Improved Separation," Frontiers in Chemistry 6(417):1-11.

Plückthun, A. (1994). "Antibodies from *Escherichia coli*," in Chapter 11 The Pharmacology of Monoclonal Antibodies, vol. 113, Rosenburg and Moore eds., Springer-Verlag, New York, pp. 269-315, 48 pages.

Presta, L.G. (1992). "Antibody Engineering," Current Opinion in Structural Biology, 2:593-596.

Ridgway, J.B.B. et al. (1996). "'Knobs-Into-Holes' Engineering of Antibody CH3 Domains for Heavy Chain Heterodimerization," Protein Engineering 9(7):617-621.

Riechmann, L. et al. (Mar. 24, 1988). "Reshaping Human Antibodies for Therapy," Nature 332:323-327.

Schaefer, W. et al. (Jul. 5, 2011, e-pub. Jun. 20, 2011). "Immunoglobulin Domain Crossover as a Generic Approach for the Production of Bispecific IgG Antibodies," Proc. Natl. Acad. Sci. U.S.A. 108(27):11187-11192.

Singh, N. et al. (2017, e-pub. Jan. 12, 2017). "Development of Adsorptive Hybrid Filters to Enable Two-Step Purification of Biologics," MABS 9(2):350-364.

Spiess, C. et al. (2015, e-pub. Jan. 27, 2015). "Alternative Molecular Formats and Therapeutic Applications For Bispecific Antibodies," Mol. Immunol. 67:95-106.

Tutt, A. et al. (Jul. 1, 1991) "Trispecific F(ab')3 Derivatives that use Cooperative Signaling Via the TCR/CD3 Complex and CD2 to Activate and Redirect Resting Cytotoxic T Cells," J. Immunol. 147(1):60-69.

Van Dijk, M.A. et al. (Aug. 2001). "Human Antibodies as Next Generation Therapeutics," Curr. Opin. Che. Biology 5(4):368-374.

(56) References Cited

OTHER PUBLICATIONS

Yigzaw, Y. et al. (2006, e-pub. Jan. 1, 2006). "Exploitation of The Adsorptive Properties of Depth, Filters For Host Cell Protein Removal During Monoclonal Antibody Purification," Biotechnology Progress 22(1):288-296.

Yu, D. et al. (Jun. 11, 2019). "Control of Antibody High And Low Molecular Weight Species By Depth Filtration-Based Cell Culture Harvesting," Biotechnology And Bioengineering 116(10):2610-2620.

Zhou, J.X. et al. (Oct. 1, 2008). "Implementation of Advanced Technologies In Commercial Monoclonal Antibody Production," Biotechnology Journal 3(9-10):1185-1200.

U.S. Appl. No. 17/767,842, Davies et al, filed Apr. 8, 2022 (not submitted herewith pursuant to the waiver of 37 C.F.R. § 1.98(a)(2)(iii) issued by the Office on Sep. 21, 2004).

U.S. Appl. No. 17/797,293, Arcadu et al, filed Aug. 3, 2022 (not submitted herewith pursuant to the waiver of 37 C.F.R. § 1.98(a)(2)(iii) issued by the Office on Sep. 21, 2004).

International Preliminary Report on Patentability, issued May 2, 2023, for PCT Application No. PCT/US2021/057100, filed Oct. 28, 2021, 14 pages.

3M Purification Inc. (Oct. 22, 2020). "Polisher ST Scale-up Capsules: Scale-Up Capsules Installation and Operation Instruction," 34-8726-1126-3, Datasheet, 82 pages.

3M Purification Inc. (Sep. 2018). "Safety Information & Installation and Operation Instructions," 34-8723-4281-0 Datasheet, 80 pages.

Amara, J. et al. (Sep. 2016). "Novel Synthetic Adsorptive Depth Filter Media for CHO Harvest Clarification," Merck Poster, 1 page.

Anonymous (Jun. 2018). MILLSTAK+® HC Pro Data Sheet, Merck, 5 pages.

Anonymous (Jun. 2020). "Prefilter Selection Guide," Merck KGaA MK_PG5156EM datasheet, 4 pages.

Arnold, T.E. (Nov. 2005). "Fluid Purification Using Charge-Modified Depth Filtration Media," BioProcess International pp. 44-49.

European Office Action, dated May 17, 2023, for European Patent Application No. 21701079.2, 6 pages.

Follman, D.K. et al. (2004). "Factorial Screening of Antibody Purification Processes Using Three Chromatography Steps Without Protein A," J. Chromatogr. A 1024(1-2):79-85.

GE Healthcare (Nov. 2013). "Instructions 71-7129-00 AF: Phenyl Sepharose High Performance; Butyl Sepharose High Performance," 16 pages.

Ghose, S. et al. (2013). "Purification of Monoclonal Antibodies by Hydrophobic Interaction Chromatography Under No-Salt Conditions," Mabs. 5(5):795-800.

Kishore, R.S.K. et al. (Feb. 2011). "Degradation of Polysorbates 20 and 80: Studies on Thermal Autoxidation and Hydrolysis," J. Pharm. Sci. 100(2):721-731.

Li, Y. (2017, e-pub. Apr. 13, 2017). "Effective Strategies for Host Cell Protein Clearance in Downstream Processing of Monoclonal Antibodies and Fc-Fusion Proteins," Protein Expression and Purification 134:96-103.

Lu, C. et al. (Jan./Feb. 2013). "Characterization of Monoclonal Antibody Size Variants Containing Extra Light Chains," mAbs 5(1):102-113.

Pall Life Sciences Data Sheet (Sep. 2004). "Pall Mustang S Capsules," PELEH/02.SH/CS/09.2004 Datasheet, 4 pages.

Tianjin, J. et al. (2018). "Research Progress in Purification Technology of Antibody Drugs in Process of Large-Scale Production," China Academic Journal 35(10):6-11. English Abstract, 6 pages.

Wang, S. et al. (2018, e-pub. Mar. 16, 2018). "Characterization of Product-Related Low Molecular Weight Impurities in Therapeutic Monoclonal Antibodies Using Hydrophilic Interaction Chromatography Coupled with Mass Spectrometry," J. of Pharmaceutical and Biomedical Analysis 154:468-475.

Xu, J. (2011). "Viral and Plasmid Transduction Systems: Methods to Modify Immune Cells for Cancer Immunotherapy," Nature Biotechnology, 29 pages.

Hester, J. et al. (Oct. 2020). "Streamlined Polishing and Viral Clearance: Using a New Hybrid, Biomimetic, Single-Use Anion Exchanger," BioProcess International 18(10):70-76.

MILLISTAK+ ® HC Pro (Sep. 9, 2020). Millipore, With English Translation. 12 pages.

METHODS TO DECREASE IMPURITIES FROM RECOMBINANT PROTEIN MANUFACTURING PROCESSES

CROSS-REFERENCE TO RELATED APPLICATIONS

This application is a continuation of International Application No. PCT/EP2021/050809, filed on Jan. 15, 2021, which claims the priority benefit of European Patent Application No. 20151994.9, filed on Jan. 15, 2020, the disclosures of each of which are hereby incorporated by reference in their entireties.

TECHNICAL FIELD

This invention relates to methods for reducing the amount of product-related impurities in a solution of monoclonal antibodies (mAbs). In particular, the methods of the invention involve the use of depth filters to reduce the amount of non-aggregate product-related impurities (NAPRIs).

BACKGROUND ART

Monoclonal antibodies (mAbs), such a bispecific antibodies (BsAbs), are an important therapeutic modality (1). Their high molecular size and sophisticated folded structure has led to mammalian cell culture being a favoured means of expressing these proteins (2).

Mammalian cell culture expression results in both product- and process-related impurities, which must be removed during purification of mAb molecules. Purification steps to remove these impurities can include centrifugation, depth filtration, Protein A chromatography, viral inactivation, cation exchange chromatography, anion exchange chromatography, a multimodal (mixed mode) chromatography, viral filtration and ultrafiltration.

Depth filters are widely used to remove process-related impurities from liquid media, thereby 'clarifying' the media, and preventing membrane fouling in subsequent purification steps. For instance, antibody-containing media that has been harvested from cell cultures are often passed through a depth filter to remove solid, insoluble components of the cell culture process, such as host cell protein (HCP) and DNA contaminants (3), and adventitious and endogenous viruses (4), prior to final filtration through a microfiltration membrane (5) or column chromatography.

Depth filters comprise porous materials such as cellulose pulps, diatomaceous earth, polyacrylic fiber and silica, and some depth filters comprise more than one layer of the porous material (6).

Depth filters have also been observed to remove product-related aggregate species through electrostatic or hydrophobic interactions, subsequent to protein A purification and viral inactivation (7).

During protein production, product-related impurities include high-order aggregation species, which are complexes comprising product aggregates. These product-related aggregates and impurities may include HCPs and DNA (4). Other non-aggregate product-related impurities include unreacted (unpaired) half antibodies, noncovalently or covalently linked homodimers, and noncovalently linked heterodimers, which are closely related to the product of interest and are challenging to remove by standard processes such as Protein A purification (8).

Bispecific heterodimeric antibodies, comprising heavy and fight chains from different monospecific monoclonal antibodies, can be produced in high yields by "knobs-into-holes" strategies (9) which bias the formation of a particular heterodimer. It is based on the principle that "knobs" (replacement of a small amino acid by a large amino acid in a region of one antibody chain) pack preferentially with "holes" (replacement of a large amino acid by a small amino acid in a corresponding region of another antibody chain), to favour selective heterodimerisation between specific chains. However, this method can produce further non-aggregate side-products, for instance resulting from false-paired knob-knob and hole-hole by-products.

There remains a need to provide methods for reducing the amount of non-aggregate product-elated impurities.

DISCLOSURE OF THE INVENTION

The present invention provides novel methods and uses for reducing the amount of non-aggregate product-related impurities in a buffered solution of monoclonal antibodies (mAbs), by using a depth filter which comprises silica and polyacrylic fiber. The inventors found that using such a depth filter led to a decrease in non-aggregate product related impurities.

As discussed herein, depth-filters are known to reduce certain process-related impurities, such as HCPs and DNAs, as well as aggregate product-related impurities, in recombinant protein manufacturing processes. However, the inventors did not expect the depth filter to reduce non-aggregate product-related impurities. At its broadest, the present invention relates to this unexpected finding.

Accordingly, one aspect of the invention provides a method of reducing the amount of non-aggregate product-related impurities (NAPRIs) in a buffered solution of monoclonal antibodies (mAbs), wherein the method comprises passing the buffered solution of monoclonal antibodies (mAbs) through a depth filter comprising silica and polyacrylic fiber, to remove a proportion of the NAPRIs from the buffered solution. The amount of NAPRIs is reduced by passing the buffered solution of mAbs through the depth filter.

In a further aspect, this invention provides a method of producing a buffered solution of monoclonal antibodies (mAbs) with a reduced amount of non-aggregate product-related impurities (NAPRIs), wherein the method comprises passing a buffered solution of monoclonal antibodies (mAbs) through a depth filter comprising silica and polyacrylic fiber, to produce the buffered solution of monoclonal antibodies (mAbs) with a reduced amount of non-aggregate product-related impurities (NAPRIs). The amount of NAPRIs is reduced by passing the buffered solution of mAbs through the depth filter.

In a further aspect, this invention provides use of a depth filter comprising silica and polyacrylic fiber to reduce the amount of non-aggregate product-related impurities (NAPRIs) in a buffered solution of monoclonal antibodies (mAbs).

In a further aspect, this invention provides a buffered solution of monoclonal antibodies (mAbs) in which the amount of non-aggregate product-related impurities (NAPRIs) has been reduced relative to the amount of the mAbs, produced by performing any of the methods of the invention, or by any of the uses of the invention.

In a further aspect, this invention provides a method of a producing a mAb, the method comprising the steps of:

(a) culturing a host cell comprising a nucleic ac encoding for a mAb so that the mAb is produced along with NAPRIs;

(b) forming a buffered solution of the mAb and NAPRIs;

(c) reducing the amount of reduced NAPRIs by performing the methods of the invention or by the uses of the invention; and optionally (d) isolating the mAb from the buffered solution.

The following embodiments are embodiments of the aspects of the invention.

In some embodiments, the buffered solution of mAbs is a concentrated buffered solution of mAbs. In some embodiments, the concentration of the concentrated buffered solution of mAbs is between 2 mg/mL and 20 mg/mL between 5 mg/mL and 15 mg/mL or between 5 mg/mL and 10 mg/mL.

In some embodiments, the mAb is a multispecific antibody, in one embodiment the mAb a bispecific antibody. In some embodiments, the mAb is an antibody fragment. In some embodiments, the mAb is an antibody fusion protein comprising an antibody or antibody fragment and another biologically active polypeptide.

In some embodiments, the buffered solution of monoclonal antibodies is passed through the depth filter at a temperature that is below ambient temperature. For instance, the temperature may be between about 4° C. and about 22° C. The temperature may be between about 10° C. and about 21° C. The temperature may be between about 15° C. and about 20° C.

The present invention allows largescale antibody purification. Large amounts of antibodies can be loaded onto the silica and polyacrylic fiber depth filter. For instance, the load can be over 100 g/m$^2$, over 200 g/m$^2$, over 300 g/m$^2$ over 500 g/m$^2$, or over 700 g/m$^2$. The load can be up to 1500 g/m$^2$, 2000 g/m$^2$, or 2500 g/m$^2$. The flow rate can be in the range of between about 1 L/min*m$^2$ to about 10 L/min*m$^2$, for example 1.5 L/min*m$^2$ to about 8 L/min*m$^2$. In preferred examples, the flow rate is in the range of between about 3 L/min*m$^2$ to about 6 L/min*m$^2$, or at about 4.3 L/min*m$^2$. The unit 'L/min*m$^2$' denotes the volume (litres) flowing through the filter per minute, per unit area (m$^2$).

Even before passage through the depth filter, the NAPRIs are present at a relatively low concentration in the initial buffered mAb solution, e.g. at least 1.5-fold, at least 2-fold, at least 5-fold, at least 10-fold, at least 20-fold, at least 50-fold, at least 100-fold, at least 1000-fold or at least 10,000-fold lower than the concentration of the mAb. This invention allows the NAPRI concentration to be reduced even further relative to the concentration of the mAb.

Similarly, the absolute amount of NAPRI (e.g. measured in moles) relative to the absolute amount of mAb is reduced (and the absolute amount of NAPRI in solution is reduced following passage through the depth filter). Moreover, the NAPRI concentration may be reduced after the solution has passed through the depth filter, relative to the NAPRI concentration before the solution passes through the depth filter (although this is not necessarily always the case, e.g. if wash fractions are included in the eluted solution, thus increasing its volume).

The reduction in NAPRI concentration relative to the mAb concentration can be expressed as a reduction in the following ratio; [mAb]-[NAPRI]. This ratio is increased after the solution has passed through the depth filter.

Typically, the non-aggregate product-related impurities (NAPRI) is a polypeptide comprised of incompletely or incorrectly assembled polypeptide chains of the mAb. In some embodiments, the NAPRI is a polypeptide lacking one or more polypeptide chains of the mAb. In some embodiments, the NAPRI is a polypeptide comprising a different polypeptide chain arrangement than the mAb. In some embodiments, the non-aggregate product-related impurities (NAPRIs) comprise a polypeptide that have a different amino acid sequence and/or different antibody chain configuration from the mAb.

In one embodiment the mAb is a multispecific antibody consisting of four different polypeptide chains and the NAPRI is a polypeptide (a) lacking one or more of said four polypeptide chains, or (b) comprising two or more of the same of said four different polypeptide chains. In one embodiment the mAb is a multispecific antibody comprising two heavy chains that are associated with each other, wherein one heavy chain comprises a knob mutation and the other heavy chain comprises a hole mutation, and the NAPRI is a polypeptide comprising two heavy chains comprising a knob mutation that are associated with each other, or two heavy chains comprising a hole mutation that are associated with each other. In one embodiment the mAb is a multispecific antibody comprising two Fab fragments, wherein a first Fab fragment comprises a first light chain comprising in N, to C-terminal direction a VL domain and a CL domain and a first heavy chain comprising in N- to C-terminal direction a VH domain and a CH1 domain; and wherein a second Fab fragment comprises either (a) a second light chain comprising in N- to C-terminal direction a VL domain and a CH1 domain and a second heavy chain comprising in N- to C-terminal direction a VH domain and a CL domain, (b) a second light chain comprising in N- to C-terminal direction a VH domain and a CH1 domain and a second heavy chain comprising in N- to C-terminal direction a VL domain and a CL domain, or (c) a second light chain comprising in N- to C-terminal direction a VH domain and a L domain and a second heavy chain comprising in N- to C-terminal direction a VL domain and a CH1 domain; and wherein the NAPRI is a polypeptide, wherein (a) the first light chain and the second heavy chain are associated, (b) the second tight chain and the first heavy chain are associated, (c) two first heavy chains are associated, (d) two second heavy chains are associated, or (e) the polypeptide lacks at least one of the first light chain, first heavy chain, second light chain and second heavy chain.

In some embodiments, the NAPRI comprises two heavy chains which are the same as each other. In some embodiments, the NAPRI comprises two heavy chains having the same amino acid sequence. In some embodiments, the NAPRIs comprise two heavy chains that are the same as each other and/or two light chains that are the same as each other. For instance, where the product is a bispecific monoclonal antibody that has been engineered to pair via knob-hole interactions, the NAPRI may comprise knob-knob and/or hole-hole false-paired chains. In some embodiments the non-aggregate product-related impurities (a) have false chain configurations; (b) have a loss of parts, optionally missing a light chain, (c) have an addition of parts, optionally wherein the impurity is a monomer with a light chain; (d) is a ¾ antibody; (e) is a light chain mispairing; (f) is a knob/knob antibody; or (g) is a hole/hole antibody, in some embodiments the NAPRI may be a light chain dimer, free light chain, a heavy chain dimer wherein one of the heavy chains is truncated, a heavy chain monomer, or a 1+1 clipping dimer.

In some embodiments, the buffered solution has a pH of about 4.0 to about 7.5. In some embodiments, the buffered solution has a pH of about 4.0 to about 7.2. In some embodiments, the buffered solution has a pH of about 4.0 to about pH 5.5. The buffered solution may comprise sodium acetate or sodium citrate. The buffered solution may comprise sodium acetate. In some embodiments, the buffered solution may comprise 150 mM sodium acetate. In some embodiments, the buffered solution may comprise 10 mM or 50 mM sodium citrate. In some embodiments, the buffered solution may comprise histidine. In some embodiments, the buffered solution may comprise acetic acid. In some embodiments, the pH of the solution is buffered with Tris.

In some embodiments, the concentration of a non-aggregate product-related impurity (NAPRI) has been measured after the amount of NAPRIs has been reduced according to the methods of the invention.

In some embodiments, the buffered solution of mAbs (or buffered solution of mAb) may have been subjected to chromatography (before the depth filter is used). In some embodiments, the buffered solution of mAbs may have been subjected to affinity chromatography, anion exchange chromatography, cation exchange chromatography or multimodal (mixed mode) chromatography. In some embodiments, the buffered solution of mAbs may have been subjected to affinity chromatography, for instance using a Protein A resin, a Protein L resin, an Fc-selective resin, a Kappa light chain-selective resin, or a Lambda light chain-selective resin. Additionally or alternatively to a previous chromatography, e.g. affinity chromatography, in some embodiments, the buffered solution of mAbs may have been subjected to ion exchange chromatography, for instance on an anion exchange or cation exchange column, or a multimodal (mixed mode) chromatography. The buffered solution mAbs may been concentrated by subjection to affinity chromatography.

The depth fitter may be a multi-layer depth filter comprising multiple levels of depth filter media. Preferably, the depth filter is a double layer depth filter. Preferably, the depth filter does not contain diatomaceous earth. The depth filter may be a Millistak+® HC Pro Synthetic Depth Filter X0SP in some embodiments.

The methods and uses of this invention may further include a step of identifying the presence or absence of NAPRI, or measuring the NAPRI concentration, in the buffered solution of mAbs after the solution has passed through the depth filter. The amount of NAPRI remaining can be measured. Similarly, the amount of mAb can be measured after the solution has passed through the depth filter, in some embodiments, the amount of NAPRI remaining can be measured by Capillary Electrophoresis SDS Page or Size Exclusion Chromatography. In some embodiments, the NAPRI is heavy chain dimer where one heavy chain is truncated; a heavy chain; or a product light chain, and its amount can be measured with Capillary Electrophoresis SDS Page in a reducing environment. In some embodiments, the NAPRI is a L-MW a 1+1 dimer (a heavy chain that has been truncated) a 1+1 clipping dimer (a heavy chain truncated and clipped in the hinge region) a hole-hole mispairing; a hole-hole mispairing; a half-hole; a light chain or alight chain dimer, and its amount can be measured with Size Exclusion Chromatography and/or with Capillary Electrophoresis SDS Page in a non-reducing environment in some embodiments, the NAPRI is a HMW, and its amount can be measured with hydrophobic interaction chromatography and/or with Capillary Electrophoresis SDS Page in a non-reducing environment. In some embodiments, the HMW NAPRI is a knob-knob mispairing. In some embodiments, the NAPRI is a heavy chain knob, or a heavy chain hole.

In some embodiments, the total concentration or amount of non-aggregate product-related impurities (NAPRIs), or a non-aggregate product-related impurity (NAPRI) is less than 40%, less than 35%, less than 30%, less than 25%, less than 20%, less than 15%, less than 14%, less than 13%, less than 12%, less than 11%, less than 10%, less than 8%, less than 8%, less than 5%, less than 4%, less than 3%, less than 2% or less than 1%.

In some embodiments, the concentration of a non-aggregate product-related impurity (NAPRI) is measured by Size Exclusion Chromatography (SEC), optionally wherein the measurement is performed using high performance liquid chromatography.

In some embodiments, the concentration of a non-aggregate product-related impurity (NAPRI) is measured by Capillary Electrophoresis SDS Page (CE-SDS), optionally wherein the measurement is performed using a LabChip device or a LabChip GXII device.

BRIEF DESCRIPTION OF FIGURES

FIG. 38 shows a LabChip (SDS-Page Equivalent) trace for the purification of second trivalent bispecific antibody with (grey) and without (black) depth filtration. The reduction in impurities as a result of depth filtration is discussed in Example 2. The areas under the labelled peaks are shown in Table 4.

DETAILED DESCRIPTION

Antibody Production and Purification

Figure 1A:
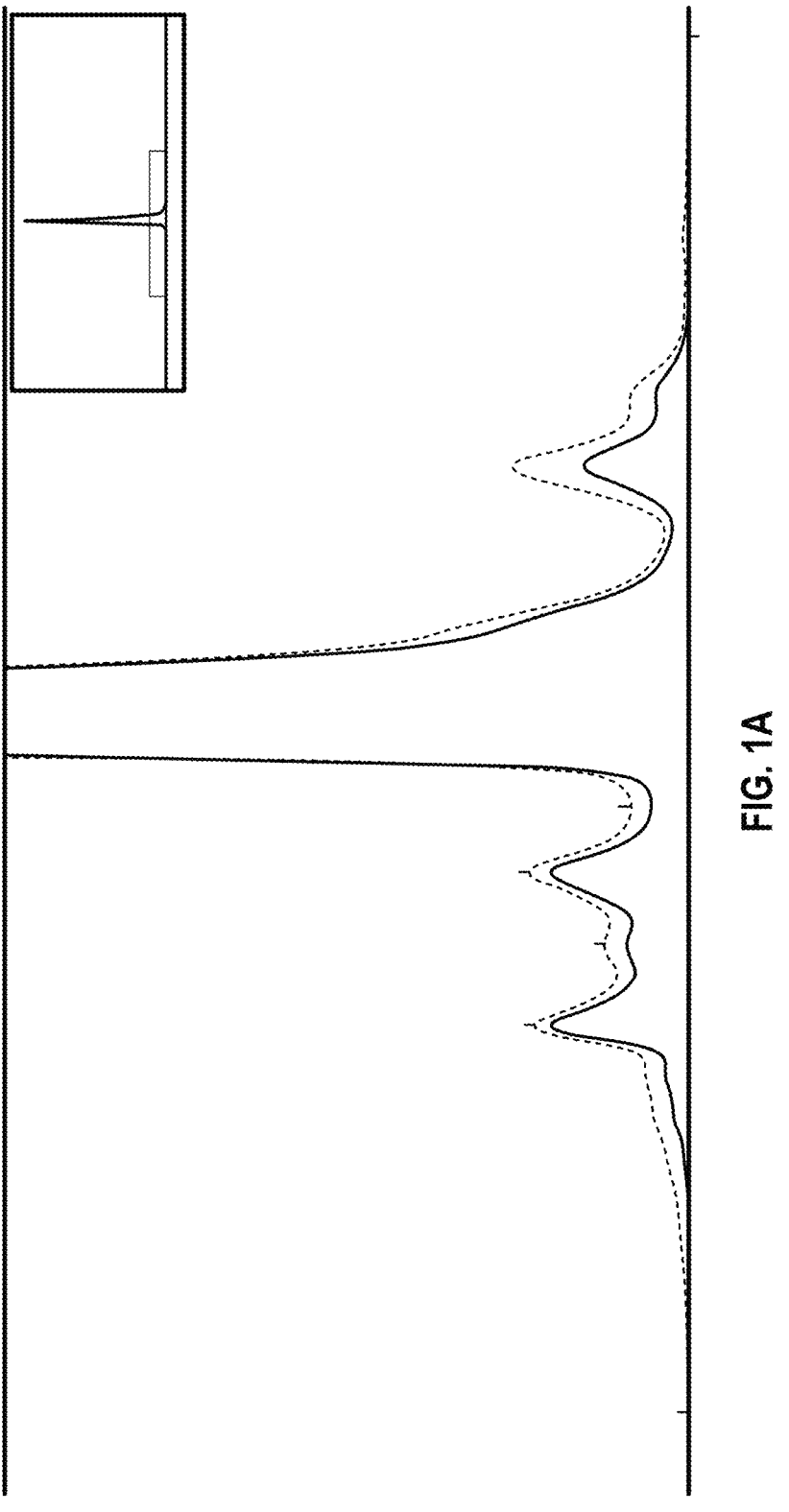
FIG. 1A shows a Size Exclusion Chromatography (SEC) trace for the purification of a first trivalent bispecific antibody comprising two heavy chain polypeptides and three light chain polypeptides with (black solid line) and without (black dashed line) depth filtration. The reduction in impurities as a result of depth filtration is discussed in Example 1.

Depth filters can be used at various stages of monoclonal antibody production/purification.

The process can comprise the following steps:

Harvest Separates cells and cell debris from protein-containing supernatant. The harvest step is typically performed using centrifugation and/or filtration;

Fc-binding/Protein A affinity chromatography. This step captures mAb molecules by preferentially binding to the Fc region at neutral pH and allows the rest of the harvested supernatant to be removed. The mAb molecules are then eluted at low pH;

Lambda light chain binding/Protein L affinity chromatography. This step captures mAb molecules by preferentially binding to the lambda light chain in the Fab region at neutral pH and allows the rest of the harvested supernatant to be removed. The mAb molecules are then eluted at low pH, Kappa light chain binding/Protein L affinity chromatography. This step captures mAb molecules by preferentially binding to the kappa light chain in the Fab region at neutral pH and allows the rest of the harvested supernatant to be removed. The mAb molecules are then eluted at low pH;

Viral inactivation: incubation of the protein A/L elution pool at low pH can inactivate adventitious viruses;

Cation exchange chromatography: This step can remove HCPs, mAb aggregates and antibody fragments, and can comprise a bind-elute or flow-through step;

Anion exchange chromatography: This step can remove DNA, leached protein A/L and other trace contaminants, and can be performed in flow-through, Viral filtration: Single-pass (dead-end) filtration with membranes designed to remove viruses; and Ultrafiltration: In this step, by passing the sample through a semi-permeable membrane (pore sizes may range between 0.1-0.01 μm), the mAb molecules can be concentrated further. If this is the final purification step, the elution buffer can be exchanged to a final formulation buffer.

Depth filtration can be used, for example, prior to viral inactivation, cation exchange chromatography, viral filtration and ultrafiltration, to remove insoluble product-related impurities, and process-related impurities as disclosed herein. Depth filtration can be used to reduce non-aggregate product-related impurities in a buffered solution of monoclonal antibodies (mAbs). In some embodiments, depth filtration can be used to reduce non-aggregate product-related impurities that are polypeptides that have a different amino acid sequence and/or different antibody chain configuration from the mAb. In some embodiments, depth filtration can be used to reduce non-aggregate product-related impurities that comprise two heavy chains which are the same as each other.

Depth filtration can also be used. In further downstream stages of the purification process for secondary clarification and haze removal, and for further removal of product-related impurities as disclosed herein. In some embodiments, depth filtration can be used to reduce non-aggregate product-related impurities in a buffered solution of monoclonal antibodies (mAbs). In some embodiments, depth filtration can be used to reduce non-aggregate product-related impurities that are polypeptides that have a different amino acid sequence and/or different antibody chain configuration from the mAb. In some embodiments, depth filtration can be used to reduce non-aggregate product-related impurities that comprise two heavy chains which are the same as each other.

All methods disclosed herein can be performed in any suitable order unless otherwise indicated herein or otherwise clearly contradicted by context.

Other Definitions

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about" whether or not explicitly indicated. The term "about" generally refers to a range of numbers that one would consider equivalent to the recited value (i.e., having the same function or result). In many instances, the term "about" may include numbers that are rounded to the nearest significant figure.

Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass all sub ranges subsumed therein. For example, a range of "1 to 10" includes any and all sub ranges between (and including) the minimum value of 1 and the maximum value of 10, that is, any and all sub ranges having a minimum value of equal to or greater than 1 and a maximum value of equal to or less than 10, e.g., 5.5 to 10.

Before describing the present invention in further detail, a number of terms will be defined. Use of these terms does not limit the scope of the invention but only serve to facilitate the description of the invention.

"Polypeptide chain arrangement" as used heroin refers to the association of the polypeptide chains within a mAb. A regular IgG antibody comprises two identical heavy chains and two identical light chains, wherein in order to form the IgG molecule, the polypeptide chains are arranged as follows: the two heavy chains are associated with each other and each one of the light chains is associated with one of the heavy chains.

As used herein the phrase "cell culture" includes cells, cell debris and colloidal particles, biomolecule of interest, HCP, and DNA.

The term "chromatography", as used herein, refers to any kind of technique which separates an analyte of interest (e.g. monoclonal antibodies (mAbs)) from other molecules present in a mixture (e.g. non-aggregate product-related impurities). Usually, the analyte of interest is separated from other molecules as a result of differences in rates at which the individual molecules of the mixture migrate through a stationary medium under the influence of a moving phase, or in bind and elute processes.

The terms "chromatography resin" or "chromatography media", are used interchangeably herein and refer to any kind of phase (e.g., a solid phase) which separates an analyte of interest (e.g. monoclonal antibodies (mAbs)) from other molecules present in a mixture (e.g. non-aggregate product-related impurities). Usually, the analyte of interest is separated from other molecules as a result of differences in rates at which the individual molecules of the mixture migrate through a stationary solid phase under the influence of a moving phase, or in bind and elute processes. Examples of various types of chromatography media include, for example, cation exchange resins, affinity resins, anion exchange resins, multimodal (mixed mode) resins (for example resins that have been functionalized with ligands capable of multiple modes of interaction such as ion exchange, hydroxyapatite, affinity, size exclusion, and hydrophobic interactions), ion exchange membranes, hydrophobic interaction resins and ion exchange monoliths.

The terms "clarification step" or "clarification" are used interchangeably herein, and generally refer to one or more steps used initially in the purification of biomolecules. The clarification step generally comprises removal of cells and/ or cellular debris using one or more steps including any of the following alone or various combinations thereof e.g. centrifugation and depth filtration, precipitation, flocculation and settling. Clarification step generally involves the removal of one or more undesirable entities and is typically performed prior to a step involving capture of the desired target molecule. Another aspect of clarification is the removal of soluble and insoluble components in a sample which may later on result in the fouling of a sterile filter in a purification process, thereby making the overall purification process more economical.

In some embodiments, a purification process additionally employs one or more "chromatography steps". Typically, these steps may be carried out, if necessary, after the separation of a target molecule from one or more undesired entities using a stimulus responsive polymer according to the present invention. In some embodiments, the chromatography step comprises affinity chromatography. In some embodiments, the affinity chromatography is Fc-binding/ Protein A affinity chromatography. In some embodiments, the affinity chromatography is Lambda light chain binding/ Protein L affinity chromatography. In some embodiments, the affinity chromatography is Kappa light chain binding/ Protein L affinity chromatography. In some embodiments, the buffered solution of mAbs may have been subjected to affinity chromatography, for instance using a Protein A resin, a Protein L resin, an Fc-selective resin, a Kappa light chain-selective resin, or a Lambda light chain-selective resin in some embodiments, the affinity chromatography is performed using a column, on which a target of antibody binding is immobilised on the column, such that the antibody is purified by affinity for its target. The terms "composition", "solution", or "sample" as used herein, refer to a mixture of a target molecule or a desired product (e.g. monoclonal antibodies (mAbs)) described herein along with one or more undesirable entities or impurities (e.g. non-aggregate product-related impurities). In some embodiments, the sample comprises feedstock or cell culture media into which the target molecule or a desired product is secreted. In some embodiments, the sample comprises a target molecule along with one or more impurities (e.g. host cell proteins, DNA, RNA, lipids, cell culture additives, cells and cellular debris). In some embodiments, the sample comprises a target molecule (e.g. monoclonal antibodies (mAbs)) along with non-aggregate product-related impurities.

The terms "Chinese hamster ovary cell protein" and "CHOP" as used interchangeably herein, refer to a mixture of host cell proteins ("HCP") derived from a Chinese hamster ovary ("CHO") cell culture. The HCP or CHOP is generally present as an impurity in a cell culture medium or lysate (e.g. a harvested cell culture fluid containing a protein or polypeptide of interest (e.g., an antibody or immunoadhesin expressed in a CHO cell). Generally, the amount of CHOP present in a mixture comprising a protein of interest provides a measure of the degree of purity for the protein of interest. Typically, the amount of CHOP in a protein mixture is expressed in parts per million relative to the amount of the protein of interest in the mixture. It can be quantified e.g. by measuring using ELISA or COBAS immunoassay.

The terms "contaminant", "impurity", and "debris", are used interchangeably herein, refer to any foreign or objectionable material, including a biological macromolecule such as a non-aggregate product-related impurities, DNA, an RNA, one or more host cell proteins (HCPs or CHOPs), endotoxins, viruses, lipids and one or more additives which may be present in a sample containing a protein or polypeptide of interest (e.g., an antibody) being separated from one or more of the foreign or objectionable molecules using the methods described herein.

It is understood that where the host cell is another mammalian cell type, an E. coli, a yeast cell, an insect cell, or a plant cell, HCP refers to the proteins, other than target proteins, found in a lysate of the host cell.

As used herein the term "depth filter" achieves filtration within the depth of the filter material A common class of such filters is those that comprise a random matrix of fibers bonded (or otherwise fixed), to form a complex, tortuous maze of flow channels. Particle separation in these filters generally results from entrapment by or adsorption to, the fiber matrix. The most frequently used depth filter media for bioprocessing of cell culture broths and other feedstocks consists of cellulose fibers, a filter aid such as diatomaceous earth (DE), and a positively charged resin binder. The depth filter used in the context of the invention is a depth filter comprising silica and polyacrylic fiber in some embodiments, the depth filter is a synthetic filter. In some embodiments, the depth filter comprises a silica filter aid, and/or polyacrylic fiber. In some embodiments, the depth filter comprises a silica filter aid, and/or polyacrylic fiber, and/or non-woven material. In some embodiments, the depth filter comprises silica and polyacrylic fiber as non-woven material. The depth filter may comprise nylon. In some embodiments, the depth filter does not contain diatomaceous earth. In some embodiments, the depth filter does not contain cellulose. Depth filter media, unlike absolute filters, retain particles throughout the porous media allowing for retention of particles both larger and smaller than the pore size. Particle retention is thought to involve both size exclusion and adsorption through hydrophobic, ionic and other interactions. The fouling mechanism may include pore blockage, cake formation and/or pore constriction. Depth filters are advantageous because they remove contaminants and also come in disposable formats thereby eliminating the validation issues. The depth filter may be a multi-layer depth filter comprising multiple levels of depth filter media which are layered in series. Preferably, the depth filter is a dual layer depth filter. Employing multiple depth filters ensures that more of the filtrate stream efficiently contacts the depth filter media, enabling a better adsorption profile for the impurities (3).

In some embodiments, the depth filter has a surface area of 23 cm$^2$ or greater, 0.11 m$^2$ or greater, 0.55 m$^2$ or greater, or of 1.1 m$^2$ or greater. In some embodiments, the buffered solution as defined in the claims has a volume of 100-1000 mL, 50-500 L, 250-2500 L, or 500-5000 L.

In some embodiments, the depth filter has a surface area of 23 cm$^2$ or greater, and the buffered solution as defined in the claims has a volume of 100-1000 mL. In some embodiments, the depth filter has a surface area of 0.11 m$^2$ or greater, and the buffered solution as defined in the claims has a volume of 50-500 L. In some embodiments, the depth filter has a surface area of 0.55 m$^2$ or greater, and the buffered solution as defined in the claims has a volume of 250-2500

L. In some embodiments, the depth filter has a surface area of 1.1 m² or greater, and the buffered solution as defined in the claims has a volume of 500-5000 L.

In some embodiments, the depth filtration is carried out at 10-1000 L, 20-800 L, 30-800 L, 40-440 L, or 50-200 L of buffered solution per m² of depth filter surface area.

As used herein, the term "synthetic", in the context of a "synthetic depth filter", means that, prior to use, the depth filter does not comprise, or comprises very little, naturally-derived materials (such as diatomaceous earth, cellulose, etc.). In other words, the depth filter consists of, or consists essentially of, synthetic materials (such as silica, poly-acrylic, nylon, etc).

The terms "isolating", "purifying", and "separating" are used interchangeably herein, in the context of purifying a target molecule (e.g. monoclonal antibodies (mAbs)) from a composition or sample comprising the target molecule and one or more impurities (e.g. non-aggregate product-related impurities), using the methods disclosed herein. In some embodiments, the degree of purity of the target molecule in a sample is increased by removing (completely or partially) one or more impurities from the sample by using the methods described herein.

The term "monoclonal antibody" or "mAb" as used herein refers to an antibody from a population of substantially homogeneous antibodies, i.e., all of the individual antibod-ies comprising the population are identical and/or bind the same epitope as each other, except for possible product-related impurities such as variant antibodies, e.g., antibodies containing naturally occurring mutations or arising during production of a monoclonal antibody preparation, such variants generally being present in minor amounts (The identical mAb molecules may be referred to as the "product" herein.) In contrast to polyclonal antibody preparations, which typically include different antibodies directed against different determinants (epitopes), each monoclonal antibody of a monoclonal antibody preparation is typically directed against the same determinant (or determinants, in the case of multispecific monoclonal antibodies) on an antigen as each other. Thus, the modifier "monoclonal" indicates the char-acter of the antibody as being obtained from a substantially homogeneous population of antibodies, and is not to be construed as requiring production of the antibody by any particular method. The term "mAb" as used herein includes antibodies, antibody fragments and antibody fusion proteins. A mAb may be monospecific or multispecific (e.g. bispe-cific). Monoclonal antibodies are comprised of different polypeptide chains. A regular IgG antibody comprises two identical heavy chains and two identical light chains. More complex antibodies, particularly multispecific antibodies, usually comprise more than two different polypeptides, which results in the issue of possible mispairings or incom-pleteness upon recombinant expression. In one embodiment of the invention the "mAb" comprises three or more differ-ent polypeptide chains.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')2, diabodies: linear antibod-ies; single-chain antibody molecules (e.g., scFv, and scFab); single domain antibodies (dAbs), and multispecific antibod-ies formed from antibody fragments. For a review of certain antibody fragments, see Holliger and Hudson, Nature Bio-technology 23:1126-1136 (2006).

"Multispecific antibodies" are monoclonal antibodies that have binding specificities for at least two different sites, i.e., different epitopes on different antigens or different epitopes on the same antigen. In certain aspects, the multispecific antibody has three or more binding specificities. Techniques for making multispecific antibodies include, but are not limited to, recombinant co-expression of two immunoglobu-lin heavy chain-light chain pairs having different specifici-ties (see Milstein and Cuello, Nature 305: 537 (1983)) and "knob-in-hole" engineering (see, e.g., U.S. Pat. No. 5,731, 168, and Atwell et al., J Mol. Biol 270:26 (1997)). Multi-specific antibodies may also be made by engineering elec-trostatic steering effects for making antibody Fc-heterodimeric molecules (see, e.g., WO 2009/089004); cross-linking two or more antibodies or fragments (see, e.g., U.S. Pat. No. 4,676,980, and Brennan et al. Science, 229: 81 (1985)); using leucine zippers to produce bi-specific anti-bodies (see. e.g. Kostelny et al., J Immunol., 148(5):1547-15531(1992) and WO 2011/034605); using the common light chain technology for circumventing the light chain mis-pairing problem (see, e.g., WO 98/50431), using "dia-body" technology for making bispecific antibody fragments (see, e.g., Hollinger at al., Proc. Natl. Acad. Sci. USA, 90:6444-6448 (1993)); and using single-chain Fv (sFv) dimers (see, e.g., Gruber et al., J Immunol., 152:5368 (1994)); and preparing trispecific antibodies as described, e.g., in Tutt et al. J. Immunol. 147: 60 (1991).

Engineered antibodies with three or more antigen binding sites, including for example, "Octopus antibodies", or DVD-Ig are also included herein (see, e.g., WO 2001/77342 and WO 20081024715). Other examples of multispecific anti-bodies with three or more antigen binding sites can be found in WO 2010/115589, WO 2010/112193, WO 2010/136172, WO 2010/145792, and WO 2013/026831. The bispecific antibody or antigen binding fragment thereof also includes a "Dual Acting FAb" or "DAF" comprising an antigen binding site that binds to a first as well as a second different antigen, or two different epitopes of the same antigen (see, e.g., US 2008/0069820 and WM 2015/095539).

Multi-specific antibodies may also be provided in an asymmetric form with a domain crossover in one or more binding arms of the same antigen specificity, i.e. by exchanging the VH/VL domains (see e.g., WO 2009/080252 and WO 2015/150447), the CH1/CL domains (see e.g., WO 2009/080253) or the complete Fab arms (see e.g., WO 2009/080251, WO 20161018299, also see Schaefer et al, PNAS. 108 (2011) 1187-1191, and Klein at al., MAbs 8 (2016) 1010-20). In one aspect, the multispecific antibody comprises a cross-Fab fragment. The term "cross-Fab frag-ment" or "xFab fragment" or "crossover Fab fragment" refers to a Fab fragment, wherein either the variable regions or the constant regions of the heavy and light chain are exchanged. A cross-Fab fragment comprises a polypeptide chain composed of the light chain variable region (VL) and the heavy chain constant region 1 (CH1), and a polypeptide chain composed of the heavy chain variable region (VH) and the light chain constant region (CL). Asymmetrical Fab arms can also be engineered by introducing charged or non-charged amino acid mutations into domain interfaces to direct correct Fab pairing, See e.g.; WO 2016/172485.

Various further molecular formats for multispecific anti-bodies are known in the art and are included herein (see e.g., Spiess et al. Mol Immunol 67 (2015) 95-108). The term "bispecific antibody" refers to an antibody that can specifi-cally bind to two different epitopes (targets).

As used herein, a "non-aggregate product-related impu-rity" or "NAPRI" is a side product of the desired "mAb", that may be comprised of incompletely or incorrectly assembled polypeptide chains of the desired mAb. In some embodiments, the NAPRI is a polypeptide lacking one or more polypeptide chains of the mAb. In some embodiments, the NAPRI is a polypeptide comprising a different polypeptide chain arrangement than the mAb. In some embodiments, the molecular weight of the NAPRI is lower than the molecular weight of the desired mAb. In one example, a desired mAb is a bispecific antibody comprising a first heavy chain and a first light chain derived from an antibody specifically binding to a first antigen, and a second heavy chain and a second light chain derived from an antibody specifically binding to a second antigen, wherein the CH3 domains of the first and second light chain are altered by the knobs-into-holes technology (Merchant A M et al. Nat Biotechnol 1998 July; 16(7):677-81.) In this example, NAPRI with incompletely assembled polypeptide chains are, e.g., antibodies missing one or more of the light chains. Also in this example, NAPRI with incorrectly assembled polypeptide chains may arise, like dimers of identical heavy chains (knob-knob dimers or hole-hole dimers) or full bispecific antibodies, wherein alight chain has paired with the wrong heavy chain resulting in formation of a non-functional binding site, NAPRIs of a mAb may be differentiated as high molecular weight ("HMW") and low molecular weight ("LMW") polypeptides. LMW polypeptides have a molecular weight lower than that of the mAb. HMW polypeptides have a molecular weight identical to or higher than the mAb (e.g. HMW 1 in FIG. 2). However, in connection with the invention and by definition NAPRIs expressly excludes aggregates. Aggregates are defined as being comprised of more than one copy of the desired mAb, for example the desired mAb associated with a light chain. Aggregates therefore include species having two or more copies of the desired mAb, for example dimers or multimeres of the product of interest. In one embodiment, the NAPRI is an LMW polypeptide. In one embodiment, the NAPRI is a HWM polypeptide.

The term "parts per million" or "ppm" are used interchangeably herein, and refer to a measure of purity of a desired target molecule (e.g. monoclonal antibodies (mAbs)) purified using a the methods disclosed herein. Accordingly, this measure can be used either to gauge the amount of a target molecule present after the purification process or to gauge the amount of an undesired entity. In some embodiments, the units "ppm" are used herein to refer to the amount of an impurity in a solution, e.g., HCP or CHOP, in nanograms/milliliter of protein of interest in milligrams/milliliter (i.e., CHOP ppm=(CHOP ng/ml)/(protein of interest mg/ml). When the proteins are dried {e.g., by lyophilization}; ppm refers to (CHOP ng)/(protein of interest mg)).

The terms "pI" or "isoelectric point" of a polypeptide, as used interchangeably herein, refer to the pH at which the polypeptide's positive charge balances its negative charge. pI can be calculated from the net charge of the amino acid residues or sialic acid residues of attached carbohydrates of the polypeptide or can be determined by isoelectric focusing.

As used herein the terms "pore size" and "nominal pore size" refer to the pore size which retains the majority of the particulate at 60-98 of the rated pore size.

In some embodiments, a "purification step" to isolate, separate or purify a desired target molecule (e.g. monoclonal antibodies (mAbs)) using the methods disclosed herein, may be part of an overall purification process resulting in a "homogeneous" or "pure" composition or sample, which term is used herein to refer to a composition or sample comprising less than 100 ppm HCP in a composition comprising the desired target molecule, alternatively less than 90 ppm, less than 80 ppm, less than 70 ppm, less than 50 ppm, less than 50 ppm, less than 40 ppm, less than 30 ppm, less than 20 ppm, less than 10 ppm, less than 5 ppm, or less than 3 ppm of HCP.

The term "salt", as used herein, refers to a compound formed by the interaction of an acid and a base. Various salts which may be used in various buffers employed in the methods described herein include, but are not limited to, acetate (e.g. sodium acetate), citrate (e.g., sodium citrate), chloride (e.g., sodium chloride), sulphate (e.g., sodium sulphate), or a potassium salt. The term "solvent", as used herein, generally refers to a liquid substance capable of dissolving or dispersing one or more other substances to provide a solution. Solvents include aqueous and organic solvents, where useful organic solvents include a non-polar solvent, ethanol, methanol, isopropanol, acetonitrile, hexylene glycol, propylene glycol, and 2,2-thiodiglycol.

The terms "target molecule", "target biomolecule", "desired target molecule" and "desired target biomolecule," are used interchangeably herein, and generally refer to a monoclonal antibody (mAb) molecule, which is desired to be purified or separated from one or more undesirable entities, e.g., one or more impurities, which may be present in a sample containing the polypeptide or product of interest.

EXAMPLES

The following examples are provided so as to provide those of ordinary skill in the art with a complete disclosure and description of how to make the compositions of the invention and how to practice the methods of the invention and are not intended to limit the scope of what the inventor regards as his invention. Efforts have been made to ensure accuracy with respect to numbers used (e.g. amounts, temperature, etc.), but some experimental errors and deviation should be accounted for. Unless indicated otherwise, temperature is in degrees C., chemical reactions were performed at atmospheric pressure or transmembrane pressure, as indicated, the term "ambient temperature" refers to approximately 25° C. and "ambient pressure" refers to atmospheric pressure. The invention will be further clarified by the following examples which are intended to be exemplary of the invention.

Example 1. Reduction in NAPRIs when Purifying a
First Trivalent Bispecific Antibody Comprising Two
Heavy Chain Polypeptides and Three Light Chain
Polypeptides In this example, a reduction of NAPRIs was observed when purifying the first trivalent bispecific antibody using depth filtration.
Materials
Millistak POD 1.1 m²; MX0SP10FS1
Millistak POD Pilotholder: MP0DPIL0T;
Millistak+HC POD Millistak+e HC Pro X0SP 1.1 m² flat seal;
MP0DADPTF Adapterkit
ÅktaAvant 150
Penstaltic Pump
Fraction vessels
Acetic acid
Sodium Acetate*3H₂O
150 mM sodium acetate pH 5.0-60 filtration buffer (pH adjusted with TRIS)

Method

The 1.1 m$^2$ depth filter was put into the Millistak+HC POD (Process scale holder) holder. Disposable adapters were connected (3× flow through & 3× blind plug adapter), and the POD was connected to the chromatographic system. The hydraulic valve was set to open, hydraulic pressure increased to 1000 PSI, after which the hydraulic valve was closed again. The experiment was carried out at a temperature range from +15° C. to +20° C.

The connectors for pressure and flow were connected, and the filter was flushed by opening the inlet valve and vent valve, and closing the outlet valve. When liquid came out through the vent valve, the vent valve was closed and the outlet valve was opened.

The system was flushed with buffer (150 mM sodium acetate pH 5.0-8.0) for 3 times the filter hold-up volumes, until pH and conductivity was constant.

The protein A pool containing the first trivalent bispecific antibody (in 150 mM sodium acetate pH 2.8), was conditioned to pH 5.0-6.0 using TRIS and was then applied to the depth filter. The mass load was set to 887 g/m$^2$ with a loading flow of 4.3 L/min*m$^2$.

The whole flow-through was collected, and analytics were performed on HCP content, host-cell DNA content, product-related impurities using appropriate analytical techniques such as size exclusion chromatography (SEC), microfluidic capillary electrophoresis (Labchip), mass spectrometry, and cobas e 411 (COBAS) or ELISA immunoassay.

Results

Figure 1B:
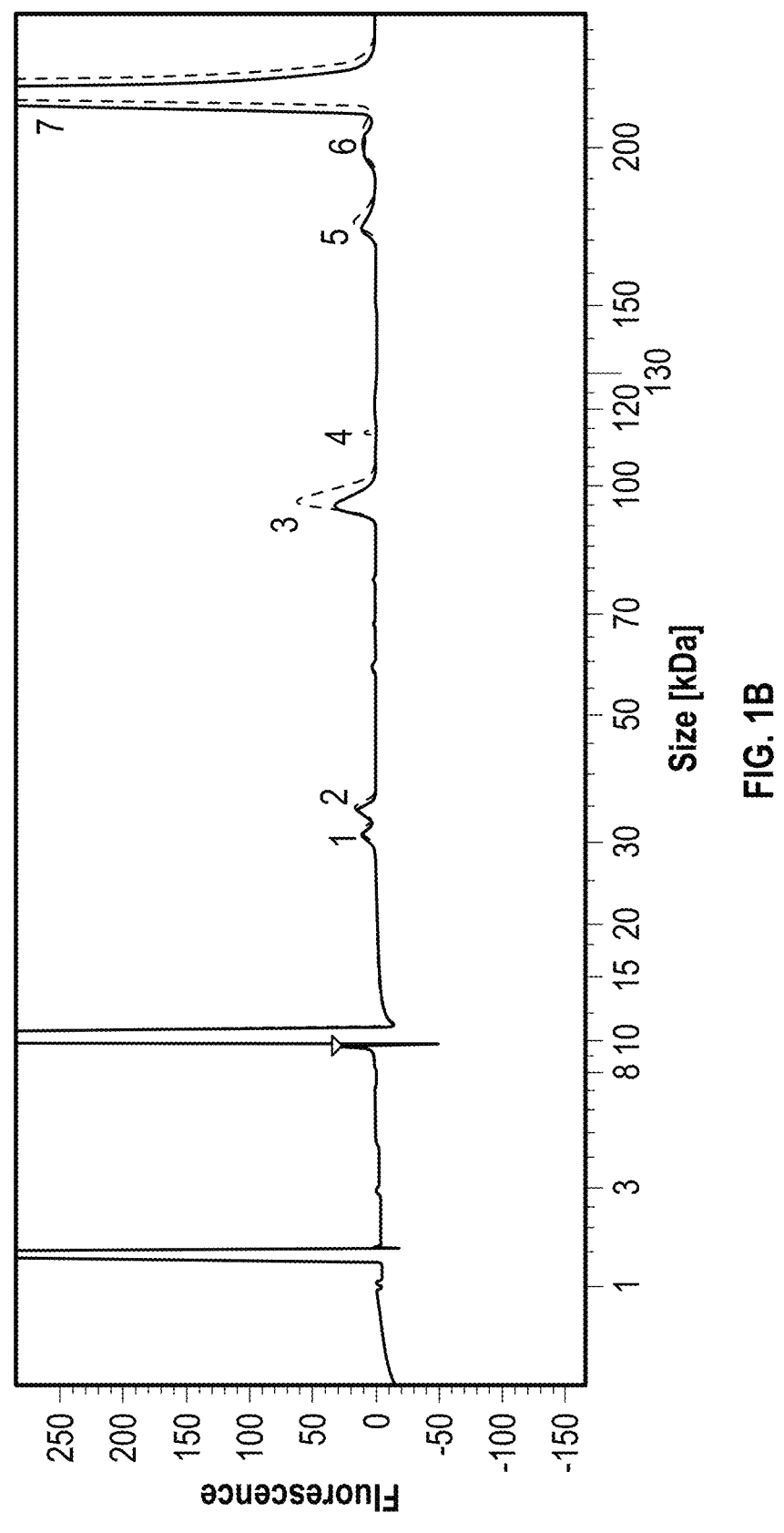
FIG. 1B shows a LabChip (SDS-Page Equivalent) trace for the purification of the first trivalent bispecific antibody with (black solid line) and without (black dashed line) depth filtration. The reduction in impurities as a result of depth filtration is discussed in Example 1. The areas under the labelled peaks are shown in Table 2.

Using the method described above, the first trivalent bispecific antibody was purified using an X0SP MX0SP10FS1 1.1 m$^2$ depth filter, and the reduction in NAPRIs, as well as other impurities, compared to purification without depth filtration (MabSelect SuRe pH 5.0), was determined via in-process control by Size Exclusion Chromatography (FIG. 1A and Table 1 below) and LabChip (SDS-PAGE equivalent) (FIG. 1B and Table 2 below).

TABLE 1

Peak areas for NAPRIs and purified first trivalent bispecific antibody as determined by SEC.

| Sample | HNWs [Area %] | HMW1 [Area %] | Mainpeak [Area %] | LMWS [Area %] |
|---|---|---|---|---|
| Load: MabSelect SuRe pH 5.0 (SEC) | 4.27 | 3.69 | 85.50 | 6.55 |
| X0SP Eluate (SEC) | 2.91 | 3.19 | 89.04 | 4.86 |
| Increase/[Reduction] | [1.36] | [0.5] | 3.54 | [1.69] |

TABLE 2

Peak areas for NAPRIs and purified first trivalent bispecific antibody as determined by LabChip

| Peak | Peak area with/without depth filtration |
|---|---|
| 7 (main product) | 91.43/86.34 |
| 6 | n/a/1.56 |
| 5 | 0.97/1.49 |
| 4 | n/a/0.17 |
| 3 | 4.86/7.79 |
| 2 | 1.59/1.57 |
| 1 | 1.15/1.08 |

As shown in Tables 1 and 2, an increase of product quality was observed, with a reduction of NAPRIs (HMW1 and LMWs) as measured by % area of the peaks in the SEC and LabChip trace.

Figure 2:
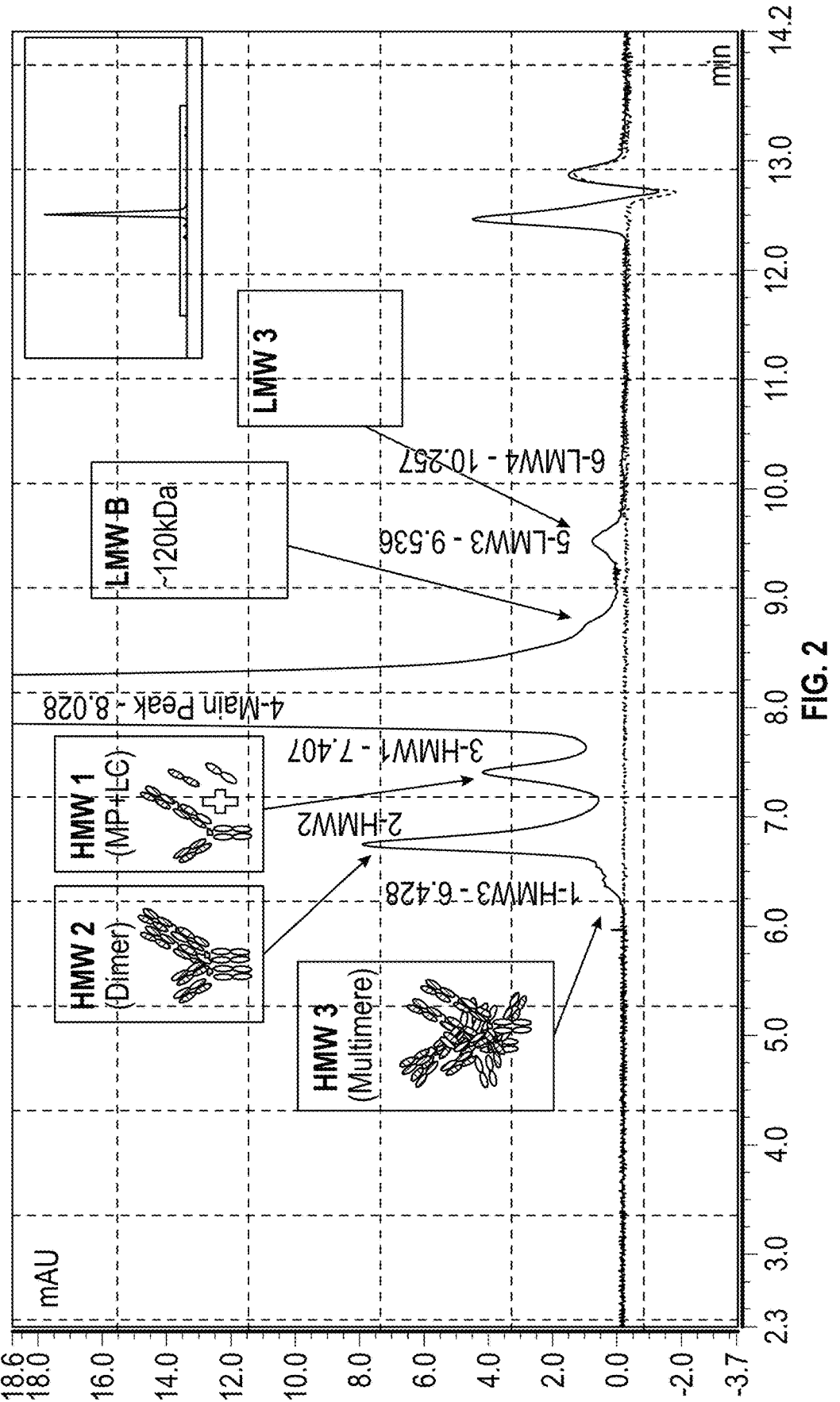
FIG. 2 shows a further Size Exclusion Chromatography (SEC) trace for the purification of the first trivalent bispecific antibody following depth filtration. The peaks are labelled with possible corresponding NAPRIs (HMW 1, LMW 8 and LMW 3) and other impurities (HMW 2, HMW 3), which is discussed in Example 1.

FIG. 2 shows a further SEC trace, where HMW1 from Table 1 was identified as a main product plus light chain and HMWs from Table 1 were identified as a dimer and multimer (non-NAPRI). LMWs from Table 1 were also identified as LMW 8 (a hole-hole NAPRI) and LMW 3 (a disaggregated monomer which has lost part of one component).

Example 2: Reduction in NAPRIs when Purifying a Second Trivalent Bispecific Antibody Comprising Two Heavy Chain Polypeptides and Three Light Chain Polypeptides In this example, a reduction of NAPRIs was observed when purifying the second trivalent bispecific antibody using depth filtration

Materials

Millistak POD 1.1 m$^2$; MX0SP10FS1

Millistak POD Pilotholder: MP0DPIL0T;

Millistak+HC POD Millistak+® HC Pro X0SP 1.1 m$^2$ flat seal;

MP0DADPTF Adapterkit

ÅktaAvant 150

Peristaltic Pump

Fraction vessels

Acetic acid

Sodium Acetate*3H$_2$O 150 mM sodium acetate pH 5.0-6.0 filtration buffer (pH adjusted with TRIS)

Method

The 1.1 m$^2$ depth filter was put into the Millistak+HC POD (Process scale holder) holder. Disposable adapters were connected (3× flow through & 3× blind plug adapter), and the POD was connected to the chromatographic system. The hydraulic valve was set to open, hydraulic pressure increased to 1000 PSI, after which the hydraulic valve was closed again. The experiment was carried out at a temperature range from +15° C. to max, +20° C. The mass load was set to 897.6 g/m$^2$ with a loading flow of 4.3 L/min*m$^2$.

The connectors for pressure and flow were connected, and the filter was flushed by opening the inlet valve and vent valve, and closing the outlet valve. When liquid came out through the vent valve, the vent valve was closed and the outlet valve was opened.

The system was flushed with buffer (150 mM sodium acetate pH 0-6.0) for 3 times the fitter hold-up volumes, until pH and cond was constant.

The protein A pool containing the second trivalent bispecific antibody (in 150 mM sodium acetate pH 2.8), was conditioned to pH 5.0-6.0 using TRIS and was then applied to the depth filter.

The whole flow-through was collected, and analytics were performed on HCP content, host-cell DNA content, product-related impurities using appropriate analytical techniques such as size exclusion chromatography (SEC), microfluidic capillary electrophoresis (Labchip), mass spectrometry, and cobas a 411 or ELISA immunoassay

Results

Figure 3A:
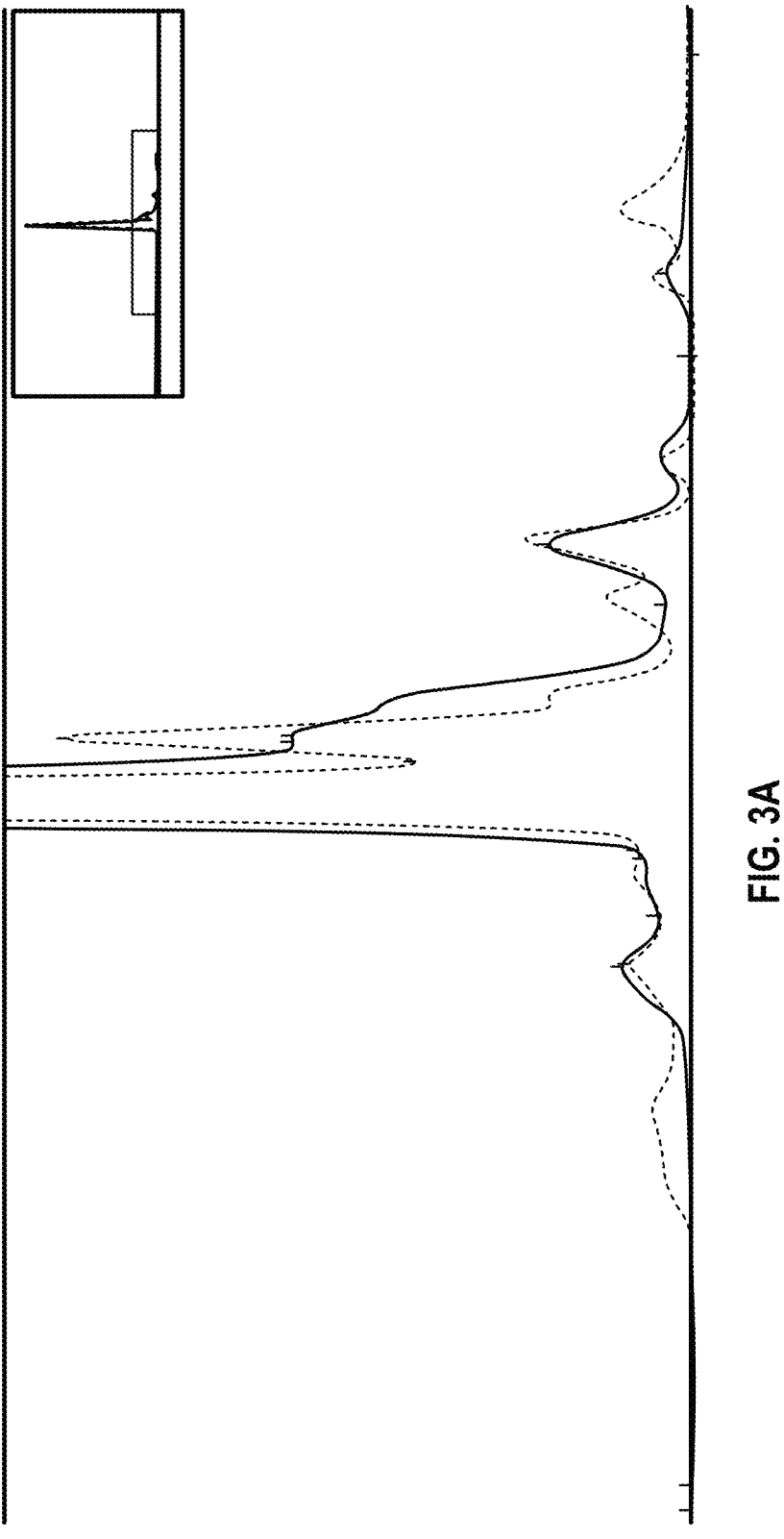
FIG. 3B shows a LabChip (SDS-Page Equivalent) trace for the purification of second trivalent bispecific antibody with (black dashed line) and without (black solid line) depth filtration. The reduction in impurities as a result of depth filtration is discussed in Example 2. The areas under the labelled peaks are shown in Table 4.
Figure 3B:
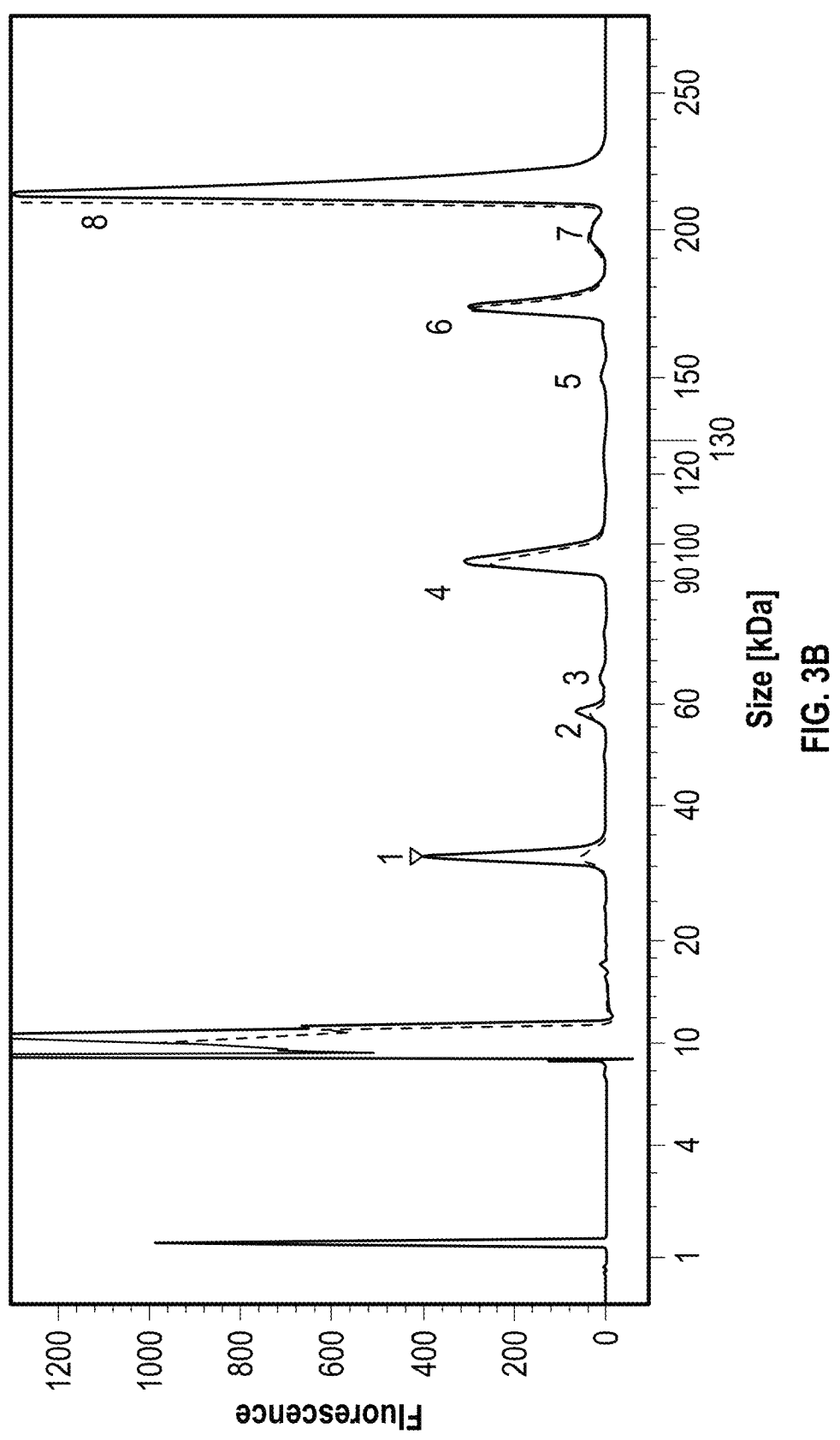

Using the method described above, the second trivalent bispecific antibody was purified using an X0SP MX0SP10FS1 1.1 m$^2$ depth filter, and the reduction in NAPRIs, as well as other impurities, compared to purification without depth filtration (MabSelect SuRe pH 5.5), was determined via in-process control by Size Exclusion Chromatography (FIG. 3A and Table 3 below) and LabChip (SDS-PAGE equivalent) (FIG. 3B and Table 4 below).

TABLE 3

Peak areas for NAPRIs and purified second trivalent bispecific antibody as determined by SEC. In total, the HMWs show a reduction of 4.59% of the total area. In total, the LMWs show a reduction of 10.59% of the total area.

| Sample | HMW3 [Area %] | HMW2 [Area %] | HMW1 [Area %] | Monomer [Area %] | LMW1 [Area %] | LMW2 [Area %] | LMW3 [Area %] |
|---|---|---|---|---|---|---|---|
| MabSelect SuRe pool pH 5.5 | 3.30 | 3.01 | 2.25 | 63.15 | 16.3 | 6.76 | 5.23 |
| X0SP Eluate Increase/ [Reduction] | — [3.30] | 2.76 [0.25] | 1.21 [1.04] | 78.34 [15.19] | 12.29 [4.01] | 4.57 [2.19] | 0.84 [4.39] |

TABLE 4

Peak areas for NAPRIs and purified second trivalent bispecific antibody as determined by LabChip.

| Peak | Peak area with/without depth filtration |
|---|---|
| 8 (main product) | 70.79/53.79 |
| 6 | 10.78/10.85 |
| 5 | n/a/0.35 |
| 4 | 13.51/16.71 |
| 3 | n/a/0.54 |
| 2 | 1.72/2.65 |
| 1 | 3.20/2.65 |

HMW1 was identified as a knob/knob NAPRI; HMW2 was identified as non-NAPRI dimers, HMW3 identified as mostly non-NAPRI aggregates. LMW1 was identified as hole/hole NAPRIs, LMW2 was identified as a hole NAPRI, and LMW3 was identified as a light chain NAPRI.

As shown in Tables 3 and 4, an increase of product quality was observed, with a reduction of NAPRIs (HMW1 and LMW1/2/3) as measured by % area of the peaks in the SEC and LabChip trace. Compared to the first trivalent bispecific antibody the product quality could be improved to an even higher extent.

Example 3. Reduction in NAPRIs when Purifying a First Antibody Fusion Protein Comprising an Antigen Binding Site and an Engineered Cytokine Variant In this example, a reduction of NAPRIs was observed when purifying the first antibody fusion protein using depth filtration.

Materials

Millistak® HC Pro X0 series μPod 23 cm$^2$: MX0SP23CL3

ÅktaAvant 150

Peristaltic Pump

Fraction vessels

Acetic acid

Sodium Acetate*3H$_2$O 150 mM sodium acetate pH 5.0-6.0 filtration buffer (pH adjusted with TRIS)

Method

The 23 cm$^2$ depth filter was preflushed with 30 ml of 150 mM sodium acetate pH 5.0-6.0 buffer, at a flow rate of 4.4 L/min*m$^2$. The protein A pool containing the first antibody fusion protein (in 150 mM sodium acetate pH 2.8) was conditioned to pH 5.0-6.0 using TRIS and was then applied to the depth filter at a flow rate of 4.4 L/min*m$^2$. The experiment was carried out at a temperature range from +15°

C. to max, +20° C. The mass load was set to 2173 g/m$^2$ with a loading flow of 1.9 L/min*m$^2$.

Fraction flow-through using an appropriate fractionation scheme was performed at a flow rate of 44 L/min*m$^2$, at the following time points 2, 4, 6, 8, 10, 15, 20, 30 and 40 minutes.

Analytics were performed on the HCP content, host-cell DNA content, product-related impurities using appropriate analytical techniques such as size exclusion chromatography (SEC), microfluidic capillary electrophoresis (Labchip), mass spectrometry, and cobas e 411 or ELISA immunoassay.

Results

Figure 4:
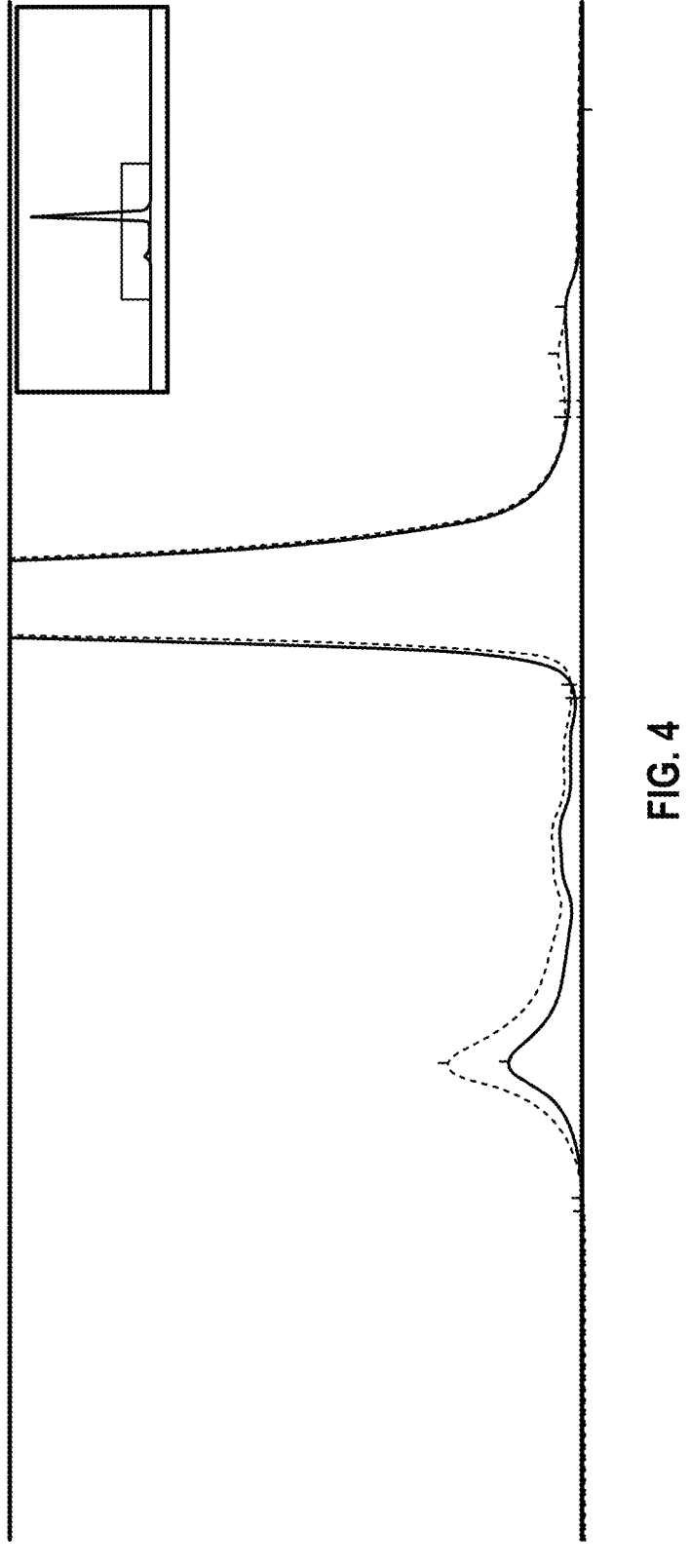
FIG. 4 shows a Size Exclusion Chromatography (SEC) trace for the purification of the first antibody fusion protein with (black solid line) and without (black dashed line) depth filtration. The reduction in impurities as a result of depth filtration is discussed in Example 3.

Using the method described above, the first antibody fusion protein was purified using an X0SP MX0SP23CL3 23 cm$^2$ depth filter, and the reduction in NAPRIs, as well as other impurities, compared to purification without depth filtration (MabSelect SuRe pH 5.5), was determined via in-process control by Size Exclusion Chromatography and LabChip (SDS-PAGE equivalent) (FIG. 4 and Table 5 below)

TABLE 5

Peak areas for NAPRIs and purified first antibody fusion protein as determined by SEC and LabChip.

| RW363 | SEC (%) | | | LabChip | |
|---|---|---|---|---|---|
| | HMW | Monomer | LMW | nr (%) | hole/knob |
| MabSelect SuRe pH 5.5 pool | 11.84 | 86.17 | 1.38 | 93.65 | 1.17 |
| Mabselect SuRe pH 5.5 after X0SP-Filter | 6.66 | 91.96 | 1.99 | 93.45 | 1.17 |
| Increase/ [Reduction] | [5.18] | 5.79 | [0.6] | [0.2] | — |

As shown in Table 5, an increase of product quality was observed, with a reduction of NAPRIs (HMWs and LMWs) as measured by % area of the peaks in the SEC and LabChip trace. The LMW is false-paired hole-hole. The HMW is false-paired knob-knob.

The difference in reduction of NAPRIs as measured by LabChip and SEC may be because Labchip can, depending on conditions, have a poorer resolution. This is because aggregates, such as Main Product+Light Chain, are mostly dissolved during sample preparation. The sample preparation is under very mild reducing conditions, in comparison to fully reducing conditions as in SEC, where it can be easier to differentiate fight and heavy chain ratios).

Example 4: Reduction in NAPRIs when Purifying the First Trivalent Bispecific Antibody after Multimodal Chromatography In this example, a reduction of NAPRIs was observed when purifying the first trivalent bispecific antibody using depth filtration, where the antibody had also been purified using multimodal chromatography Materials Millistak® HC Pro X0 series μPod 23 cm$^2$ MX0SP23CL3
Capto Adhere ImpRes chromatography column
ÅktaAvant 160
Peristaltic Pump
Fraction vessels
Acetic acid
Sodium Acetate*3H$_2$O
50 mM Sodium citrate pH 4.0 filtration buffer Method The 23 cm$^2$ depth filter was preflushed with 30 mL of 150 mM sodium acetate pH 5.0-6.0 buffer, at a flow rate of 10 mL/min (which is 4.3 L/min*m$^2$). The method was carried out at a temperature range from +15° C. to max, +20° C. The mass loads were set to 759 g/m$^2$ with a loading flow of 4.3 L/min*m$^2$.

Two different purification method steps were subsequently performed:

(i) A protein A pool containing the first trivalent bispecific antibody was then applied to the depth filter at a flow rate of 10 mL/min (filtration buffer 50 mM sodium citrate pH 4.0). The eluate was then passed through a Capto Adhere ImpRes multimodal anion exchange column (elution buffer 50 mM sodium citrate pH 6.0-50 mM sodium citrate pH 3.0; gradient 25CV), and the subsequent eluate was applied to the depth filter at a flow rate of 10 mL/min (filtration buffer 50 mM sodium citrate pH 4.0); or (ii) A protein A pool containing the first trivalent bispecific antibody was passed through a Capto Adhere ImpRes multimodal anion exchange column (elution buffer 50 mM sodium citrate pH 6.0-50 mM sodium citrate pH3.0; gradient 25CV), and the subsequent eluate was applied to the depth filter at a flow rate of 10 mL/min (filtration buffer 50 mM sodium citrate pH 4.0).

Following either method, fraction flow-through using an appropriate fractionation scheme was performed at a flow rate of 10 mL/min, at the following time points: 2, 4, 6, 8, 10, 15, 20, 30 and 40 minutes.

Analytics were performed on the HCP content, host-cell DNA content, product-related impurities using appropriate analytical techniques such as size exclusion chromatography (SEC), microfluidic capillary electrophoresis (Labchip); mass spectrometry, and cobas e 411 or ELISA immunoassay.

Results

The first trivalent bispecific antibody was purified using an X0SP MX0SP23CL3 23 cm$^2$ depth filter, whereby an multimodal anion exchange chromatography (Capto Adhere ImpRes) step was performed after protein A chromatography, and filtration was performed either after each step, or after the multimodal anion exchange chromatography step.

The reduction in NAPRIs, as well as other impurities, was determined via in-process control by Size Exclusion Chromatography (Table 6 below).

TABLE 6

Changes in peak areas for NAPRIs purified first trivalent bispecific antibody (measured with percentage points) as determined by SEC. (LMW is false-paired hole-hole. HMW is false-paired knob-knob)

| Elution buffer | Filter after ... | Fiter Buffer & pH | Reduction in precipitation/ turbidity? | Depth filter type and dimensions | Increase in main peak; Reduction in HMW/LMW |
|---|---|---|---|---|---|
| 50 mM Sodium Cirate pH 6.0-50 mM Sodium Citrate pH 3.0 Elutiontype: gradient 25 CV | Capto Adhere ImpRes (no filtration after Protein A) | 50 mM Sodium Citrate pH 4.0 | No turbidity or precipitation occurred HCP red": 98.5% (ng/mg) | Millistak + ® HC Pro Synthetic Depth Filters X0SP MX0SP230L3 23 cm$^2$ | Main peak inc 0.53 pp (SEC): HMW red". 0.14 pp LMW red": 0.16 pp Filter load: 97.34 pp Monomer (SEC) Filtrate: 97.87 pp Monomer (SEC) |
| 50 mM Sodium Cirate pH 6.0-50 mM Sodium Citrate pH 3.0 Elutiontype: gradient 25 CV | Protein A (1. Filtration) Capto Adhere ImpRes (2. Filtration) | 50 mM Sodium Citrate pH 5.5 | No turbidity or precipitation occurred HCP red": 82.9% (ng/mg) | Millistak + ® HC Pro Synthetic Depth Filters X0SP MX0SP230L3 23 cm$^2$ | Main peak inc 0.53 pp (SEC): HMW red". 0.14 pp LMW red": 0.16 pp Filter load: 97.34 pp Monomer (SEC) Filtrate: 97.87 pp Monomer (SEC) |

As shown in Table 6, an increase of product quality was observed, with a reduction of NAPRIs (HMWs and LMWs) as measured by % area of the peaks in the SEC trace. Depth filtration hence appears to reduce NAPRIs when preceded by protein A chromatography, multimodal chromatography, or a combination of the two.

Example 5: Reduction in NAPRIs when Purifying a Third Trivalent Bispecific Antibody Comprising Two Heavy Chain Polypeptides and Three Light Chain Polypeptides in this example, two samples with different pH values were considered. A reduction of NAPRIs was observed when purifying the third trivalent bispecific antibody using depth filtration at both pH 5.5 and pH 7.2

Materials

Millistak® HC Pro X0 series µPod 23 cm: MX0SP23CL3

ÅktaAvant 150

Penstaltic Pump

Fraction vessels

Acetic acid

Sodium Acetate*3H$_2$O 150 mM sodium acetate pH 5.0-6.0 filtration buffer (pH adjusted with TRIS)

25 mM Tris/Tris-HCl, 25 mM sodium chloride, pH 7.2

Method

The 23 cm$^2$ depth filter was preflushed with 30 mL of 150 mM sodium acetate pH 5.0-6.0 buffer, at a flow rate of 10 mL/min.

The method was carried out at a temperature range from +15° C. to max, +20° C. The mass loads were set to 822/m$^2$ @pH 5.5 and 853 g/m$^2$ @pH 7.2 with a loading flow of 4.3 L/min*m$^2$.

The protein A pool containing the third trivalent antibody protein (in 150 mM sodium acetate pH 2.8) was conditioned to pH 5.5 or pH 7.2 using TRIS and was then applied to the depth filter at a flow rate of 10 mL/min.

Fraction flow-through using an appropriate fractionation scheme was performed at a flow rate of 10 mL/min, at the following time points: 2, 4, 6, 8, 10, 15, 20, 30 and 40 minutes.

Analytics were performed on the HCP content, host-cell DNA content, product-related impurities using appropriate analytical techniques such as size exclusion chromatography (SEC).

Results

Using the method described above, the third trivalent antibody protein was purified using an X0SP MX0SP23CL3 23 cm$^2$ depth filter, and the reduction in NAPRIs, as well as other impurities, compared to purification without depth filtration (MabSelect SuRe pH), was determined via in-process control by Size Exclusion Chromatography (Table 6).

TABLE 6

Peak areas for NAPRIs and purified third trivalent antibody protein as determined by SEC.

| LB015 | SEC (%) | | |
|---|---|---|---|
| | HMW | Monomer | LMW |
| MabSelect SuRe pH 5.5 pool | 9.7 | 74.7 | 15.0 |

TABLE 6-continued

Peak areas for NAPRIs and purified third trivalent antibody protein as determined by SEC.

| LB015 | SEC (%) | | |
|---|---|---|---|
| | HMW | Monomer | LMW |
| Mabselect SuRe pH 5.5 after X0SP-Filter | 7.8 | 83.9 | 8.3 |
| Increase/ [Reduction] | [1.9] | 9.2 | [6.7] |
| MabSelect SuRe pH 7.2 pool | 9.8 | 74.8 | 14.9 |
| Mabselect SuRe pH 7.2 after X0SP-Filter | 7.88 | 84.7 | 7.4 |
| Increase/ [Reduction] | [1.9] | [9.9] | [7.5] |

As shown in Table 6, an increase of product quality was observed, with a reduction of NAPRIs (HMWs and LMWs) as measured by % area of the peaks in the SEC trace. The HMW NAPRIs were identified as non-covalent knob-knob species. The LMW NAPRIs were identified as light chain-dimers and free tight chains.

Example 6: Reduction in NAPRIs when Purifying a Fourth Trivalent Bispecific Antibody Comprising Two Heavy Chain Polypeptides and Three Fight Chain Polypeptides In this example, two samples with different pH values were considered. A reduction of NAPRIs was observed when purifying the fourth trivalent bispecific antibody using depth filtration at pH 5.5 and 7.2.

Materials

Millistak® HC Pro X0 series µPod 23 cm$^2$: MX0SP23CL3

ÅktaAvant 150

Peristatic Pump

Fraction vessels

Acetic acid

Sodium Acetate*3H$_2$O 150 mM sodium acetate pH 5.0-6.0 filtration buffer (pH adjusted with TRIS)

25 mM Tris/Tris-HCl, 25 mM sodium chloride, pH 7.2

Method

The 23 cm$^2$ depth filter was preflushed with 30 ml of 150 mM sodium acetate pH 5.0-6.0 buffer, at a flow rate of 10 mL/min.

The experiment was carried out at a temperature range from +15° C. to max, +20° C. The mass loads were set to 848 g/m$^2$ pH 5.5 and 838 g/m$^2$ @ pH 7.2 with a loading flow of 4.3 L/min*m$^2$.

The protein A pool containing the fourth trivalent anti-body protein (in 150 mM sodium acetate pH 2.8) was conditioned to pH 5.5 or 7.2 using TRIS and was then applied to the depth filter at a flow rate of 10 mL/min.

Fraction flow-through using an appropriate fractionation scheme was performed at a flow rate of 10 mL/min, at the following time points: 2, 4, 8, 8, 10, 15, 20, 30 and 40 minutes.

Analytics were performed on the HCP content, host-cell DNA content, product-related impurities using appropriate analytical techniques such as size exclusion chromatography (SEC).

Results

Using the method described above, the fourth trivalent antibody protein was purified using an X0SP MX0SP23CL3 23 cm$^2$ depth filter, and the reduction in NAPRIs, as well as other impurities, compared to purification without depth filtration (MabSelect SuRe pH1), was determined via in-process control by Size Exclusion Chromatography (Table 7).

TABLE 7

Peak areas for NAPRIs and purified fourth trivalent antibody protein as determined by SEC.

| AW013 | SEC (%) | | |
|---|---|---|---|
| | HMW | Monomer | LMW |
| MabSelect SuRe pH 5.5 pool | 11.4 | 72.5 | 16.1 |
| Mabselect SuRe pH 5.5 after X0SP-Filter | 8.7 | 88.4 | 2.9 |
| Increase/ [Reduction] | [2.7] | 15.9 | [13.2] |
| MabSelect SuRe pH 7.2 pool | 11.3 | 74.9 | 13.8 |
| Mabselect SuRe pH 7.2 after X0SP-Filter | 8.6 | 87.0 | 4.5 |
| Increase/ [Reduction] | [3.0] | 12.1 | [9.3] |

As shown in Table 7, an increase of product quality was observed, with a reduction of NAPRIs (HMWs and LMWs) as measured by % area of the peaks in the SEC trace. The HMW NAPRIs were identified as knob-knob species. The LMW NAPRIs were identified as light chain-dimer and free light chain species.

Numbered Paragraphs:

1. A method of reducing the amount of non-aggregate product-related impurities (NAPRIs) in a buffered solution of monoclonal antibodies (mAbs), wherein the method comprises passing the buffered solution of monoclonal antibodies (mAbs) through a synthetic depth filter comprising silica and polyacrylic fiber, to remove a proportion of the NAPRIs from the buffered solution.

2. A method of producing a buffered solution of monoclonal antibodies (mAbs) with a reduced amount of non-aggregate product-related impurities (NAPRIs), wherein the method comprises passing a buffered solution of monoclonal antibodies (mAbs) through a synthetic depth filter comprising silica and polyacrylic fiber, to produce the buffered solution of monoclonal antibodies (mAbs) with a reduced amount of non-aggregate product-related impurities (NAPRIs).

3. Use of a synthetic depth filter comprising silica and polyacrylic fiber to reduce the amount of non-aggregate product-related impurities (NAPRIs) in a buffered solution of monoclonal antibodies (mAbs).

4. The method according to any one of the preceding paragraphs, or the use according to paragraph 3, wherein the mAb is a multispecific antibody.

5. The method according to any one of the preceding paragraphs, or the use according to any one of the preceding paragraphs, wherein the mAb is an antibody fusion protein comprising an antibody or antibody fragment and another biologically active polypeptide.

6. The method according to any one of the preceding paragraphs, or the use according to any one of the preceding paragraphs, wherein the NAPRI is a polypeptide comprised of incompletely or incorrectly assembled polypeptide chains of the mAb.

7. The method according to any of the preceding paragraphs, or the use according to any one of the preceding paragraphs, wherein the NAPRI is a polypeptide lacking one or more polypeptide chains of the mAb.

8. The method according to any of the preceding paragraphs, or the use according to any one of the preceding paragraphs, wherein the NAPRI is a polypeptide comprising a different polypeptide chain arrangement than the mAb.

9. The method according to any one of paragraphs 1-6, or the use according to any one of paragraphs 3-6 wherein the NAPRI comprises two heavy chains having the same amino acid sequence.

10. The method according to any one of the preceding paragraphs, or the use according to any one of the preceding paragraphs, wherein the buffered solution of mAbs has been subjected to affinity chromatography.

11. The method according to any one of the preceding paragraphs, or the use according to any one of the preceding paragraphs, wherein the depth filter is a multi-layer depth filter comprising multiple levels of depth filter media.

12. The method according to any one of the preceding paragraphs, or the use according to any one of the preceding paragraphs, wherein the depth filter does not contain diatomaceous earth.

13. The method according to any one of the preceding paragraphs, or the use according to any one of the preceding paragraphs, further comprising measuring the NAPRI concentration in the buffered solution of mAbs after it has passed through the depth filter.

14. A buffered solution of monoclonal antibodies (mAbs) in which the amount of non-aggregate product-related impurities (NAPRIs) has been reduced relative to the amount of the mAbs, produced by performing the method according to any one of the preceding claims, or by the use according to any one of the preceding claims.

15. A method of producing a mAb, the method comprising the steps of (a) culturing a host cell comprising a nucleic acid encoding for a mAb so that the mAb is produced along with NAPRIs;

(b) forming a buffered solution of the mAb and NAPRIs;

(c) reducing the amount of NAPRIs by performing the method according to any one of the preceding claims, or by the use according to any one of the preceding claims on the buffered solution of mAb and NAPRIs, and (d) isolating the mAb from the buffered solution.

REFERENCES 1. van Dijk, M, A.; van de Winkel, J. G. Human antibodies as next generation therapeutics. Curr. Opin. Chem. Biol. 2001, 5 (4), 368-74.

2. Chadd, H. E.; Chamow, S. M. Therapeutic antibody expression technology Curr. Opin. Biotechnol. 2001, 12, 188-194.

3. Yigzaw et al Exploitation of the Adsorptive Properties of Depth Filters for Host Cell Protein Removal during Monoclonal Antibody Purification. Biotechnol Prog. 2006, 22, 288-298.

4. Singh et al. Development of adsorptive hybrid filters to enable two-step purification of biologics. MABS 2017, VOL 9, NO. 2, 350-384.

5. Badmington, F. Prefiltration technology. In Filtration in the Biopharmaceutical Industry; Meltzer. T. H., Jornitz, M. W, Eds.; Marcel Dekker. New York. 1998; pp 783-817.

6. Onur at al. Multi-Layer Filters: Adsorption and Filtration Mechanisms for improved Separation. Frontiers in Chemistry 2018 Volume 6 Article 417.

7. Nguyen at al. Improved HCP Reduction Using a New, All-Synthetic Depth Filtration Media Within an Antibody Purification Process. Biotechnol J. 2018, 1700771.

8. Giese et al. Bispecific antibody process development: Assembly and purification of knob and hole bispecific antibodies. Biotechnol Prog., 34:397-404, 2018.

9. Ridgway et al, 'Knobs-into-holes' engineering of antibody CH3 domains for heavy chain heterodimerization Protein Engineering vol. 9 no. 7 pp. 817-821, 1998

10. Klein et al. The use of CrossMAb technology for the generation of bi- and multispecific antibodies. MABS. 2016, VOL 8. NO. 6, 1010-1020.

The invention claimed is:

1. A method of producing a buffered solution of monoclonal antibodies (mAbs) with a reduced amount of non-aggregate product-related impurities (NAPRIs), the method comprising passing an initial buffered solution comprising: (a) mAbs, and (b) NAPRIs, through a synthetic depth filter comprising silica and polyacrylic fiber to produce the buffered solution of mAbs with the reduced amount of NAPRIs, wherein the NAPRIs comprise incompletely or incorrectly assembled mAb polypeptides, wherein the NAPRIs comprise high molecular weight (HMW) polypeptides having a molecular weight higher than the mAb, wherein the NAPRIs do not comprise aggregates, and wherein the reduced amount of NAPRIs is with respect to the amount of NAPRIs in the initial buffered solution before it has passed through the synthetic depth filter comprising silica and polyacrylic fiber.

2. The method of claim 1, wherein the mAb is a multi-specific antibody.

3. The method of claim 1, wherein the mAb is an antibody fusion protein comprising an antibody or antibody fragment and another biologically active polypeptide.

4. The method of claim 1, wherein the initial buffered solution of mAbs is passed through the depth filter at a temperature that is between 4° C. and 22° C.

5. The method of claim 1, wherein the NAPRI is a polypeptide lacking one or more polypeptide chains of the mAb and/or the NAPRI is a polypeptide comprising a different polypeptide chain arrangement than the mAb.

6. The method of claim 1, wherein the NAPRI comprises two heavy chains having the same amino acid sequence.

7. The method of claim 1, wherein the depth filter is a dual layer depth filter.

8. The method of claim 1, wherein the depth filter does not contain diatomaceous earth.

9. The method of claim 1, further comprising measuring the NAPRI concentration in the buffered solution of mAbs, wherein the NAPRI concentration is measured by Size Exclusion Chromatography (SEC) and/or with Capillary Electrophoresis SDS Page in a non-reducing environment.

10. The method of claim 1, wherein the initial buffered solution of mAbs has been subjected to chromatography before passing through the synthetic depth filter, and wherein the chromatography comprises one or more of ion exchange chromatography, anion exchange column, a cation exchange column, or multimodal (mixed mode) chromatography.

11. The method of claim 1, wherein the initial buffered solution of mAbs is passed through the depth filter at a temperature of between 10° C. and 21° C., or between 15° C. and 20° C.

12. The method of claim 1, wherein the initial buffered solution of mAbs is passed through the depth filter at mass load of in the range of 100 $g/m^2$ to 2500 $g/m^2$, 300 $g/m^2$ to 2000 $g/m^2$, or 500 $g/m^2$ to 1500 $g/m^2$.

13. The method of claim 1, wherein the initial buffered solution of mAbs has a pH in the range of 4.0 to 7.5, 4.0 to 7.2, or 4.0 to 5.5 when it passes through the depth filter.

14. The method of claim 1, wherein the initial buffered solution of mAbs is passed through the depth filter at a flow rate in the range of 1 $L/min*m^2$ to 10 $L/min*m^2$, 1.5 $L/min*m^2$ to 8 $L/min*m^2$, or at a flow rate that is 4.3 $L/min*m^2$.

15. The method of claim 1, further comprising the step of isolating the mAbs from the buffered solution of mAbs.

* * * * *